(12) United States Patent
Jain et al.

(10) Patent No.: US 9,562,914 B2
(45) Date of Patent: Feb. 7, 2017

(54) MICROFLUIDIC DEVICE FOR REAL-TIME CLINICAL MONITORING AND QUANTITATIVE ASSESSMENT OF WHOLE BLOOD COAGULATION

(71) Applicant: President and Fellows of Harvard College, Cambridge, MA (US)

(72) Inventors: Abhishek Jain, Roslindale, MA (US); Anna Waterhouse, Brookline, MA (US); Mike Super, Lexington, MA (US); Donald E. Ingber, Boston, MA (US); Daniel C. Leslie, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/028,667

(22) PCT Filed: Oct. 16, 2014

(86) PCT No.: PCT/US2014/060956
§ 371 (c)(1),
(2) Date: Apr. 11, 2016

(87) PCT Pub. No.: WO2015/102726
PCT Pub. Date: Jul. 9, 2015

(65) Prior Publication Data
US 2016/0258968 A1    Sep. 8, 2016

Related U.S. Application Data

(60) Provisional application No. 61/891,732, filed on Oct. 16, 2013.

(51) Int. Cl.
*G01N 33/49* (2006.01)
*G01N 33/86* (2006.01)
(Continued)

(52) U.S. Cl.
CPC ........... *G01N 33/86* (2013.01); *B01L 3/50273* (2013.01); *G01N 33/4905* (2013.01);
(Continued)

(58) Field of Classification Search
CPC .............................. G01N 33/49; G01N 33/86
(Continued)

(56) References Cited

U.S. PATENT DOCUMENTS 5,039,617 A    8/1991   McDonald et al.
5,504,011 A    4/1996   Gavin et al.
(Continued)

FOREIGN PATENT DOCUMENTS

WO    2010/077784    7/2010

OTHER PUBLICATIONS

Gilbert, R. J. et al, ASAIO Journal 2007, 53, 447-455.*
(Continued)

*Primary Examiner* — Arlen Soderquist
(74) *Attorney, Agent, or Firm* — Nixon Peabody LLP

(57) ABSTRACT

In accord with one aspect, a microfluidic coagulation assessment device defining a plurality of microchannels is provided, wherein a blood sample is driven through the microchannels at a substantially constant flow rate and a controller is configured to, in combination with a timer and a pressure sensing device, determine a first pressure value (or flow value) at an initiation of flow, a first time ($T_{pg}$) at which a second pressure value is about twice the determined first pressure value, and a second time ($T_{pf}$) at which a third pressure value is about $(1+e)$ times the determined first pressure value and establish a subject coagulation model predictive of channel occlusion therefrom. In another aspect, the blood sample is driven through the microchannels at a substantially constant pressure and a controller is configured
(Continued)

to, in combination with a timer and a flow sensing device make the determination based on flow rate.

63 Claims, 15 Drawing Sheets

(51) Int. Cl.
  *B01L 3/00* (2006.01)
  *G06F 19/24* (2011.01)
(52) U.S. Cl.
  CPC ........ *G06F 19/24* (2013.01); *B01L 2200/146* (2013.01); *B01L 2300/0627* (2013.01); *B01L 2300/08* (2013.01); *B01L 2300/0861* (2013.01); *B01L 2400/0478* (2013.01)
(58) Field of Classification Search
  USPC .............................................. 422/73; 436/69
  See application file for complete search history.

(56) References Cited

U.S. PATENT DOCUMENTS

| | | | |
|---|---|---|---|
| 6,582,284 B2 * | 6/2003 | Bonachera | B24B 5/04 451/307 |
| 7,291,310 B2 | 11/2007 | Martin et al. | |
| 7,439,069 B2 | 10/2008 | Nippoldt et al. | |
| 8,318,109 B2 * | 11/2012 | Saltsman | B01F 5/0473 422/400 |
| 8,961,903 B2 * | 2/2015 | Sadaba Champetier De Ribes | B01L 3/5027 422/500 |
| 2005/0272159 A1 * | 12/2005 | Ismagilov | B01F 5/0646 436/34 |
| 2009/0054753 A1 | 2/2009 | Robinson et al. | |
| 2010/0233026 A1 * | 9/2010 | Ismagliov | B01F 5/0646 422/68.1 |
| 2011/0039285 A1 * | 2/2011 | Sadaba Champetier De Ribes | B01L 3/5027 435/13 |

OTHER PUBLICATIONS

Runyon M. K. et al, Journal of the American Chemical Society 2008, 130, 3458-3464.*
Gutierrez, E. et al, Lab on a Chip 2008, 8, 1486-1495.*
Chau, L. et al, Lab on a Chip 2009, 9, 1897-1902.*
Prentner, S. et al, Microsystem Technologies 2010, 16, 1091-1096.*
Tsai, M. et al, Journal of Clinical Investigation 2012 122 408-418.*
Li, M. et al, Lab on a Chip 2012, 12, 1355-1362.*
Muthard, R. W. et al, Lab on a Chip 2013, 13, 1883-1891.*
International Search Report and Written Opinion mailed Aug. 19, 2015 which issued in corresponding International Patent Application No. PCT/US2014/060956 (19 pages).

* cited by examiner

| | | 75 | 150 | 350 | 750 | 1250 | 2500 | |
|---|---|---|---|---|---|---|---|---|
| Heparin Conc. [U/ml] | 0 | NA | NA | 0.99 | NA | 0.99 | NA | PRESSURE |
| | 0.1 | NA | NA | 0.98 | NA | 0.99 | NA | |
| | 0.25 | 0.79 | 0.89 | 0.97 | 0.97 | 0.96 | 0.89 | |
| | 0.5 | 0.65 | 0.84 | 0.86 | 0.92 | 0.93 | 0.83 | |
| | 1 | NA | NA | 0.94 | NA | 0.94 | NA | |
| | | \multicolumn{6}{c}{Shear Rate [sec$^{-1}$]} | |
| | | 75 | 150 | 350 | 750 | 1250 | 2500 | |
| Heparin Conc. [U/ml] | 0 | NA | NA | 0.99 | NA | 0.99 | NA | INFUSION |
| | 0.1 | NA | NA | 0.99 | NA | 0.97 | NA | |
| | 0.25 | NA | 0.91 | 0.92 | 0.98 | 0.86 | 0.9 | |
| | 0.5 | NA | 0.77 | 0.76 | 0.88 | 0.83 | 0.82 | |
| | 1 | NA | NA | 0.84 | NA | 0.89 | NA | |

FIGURE 6

| | | Shear Rate [sec$^{-1}$] | | | Heparin [U/ml] | |
|---|---|---|---|---|---|---|
| | | 350 | 1250 | | 0.25 | 0.5 |
| Clotting Times | $T_{pq}$ | 0.98 | 0.86 | | 0.99 | 0.99 |
| | $T_{pf}$ | 0.97 | 0.91 | | 0.96 | 0.97 |
| | $T_{qg}$ | 0.99 | 0.97 | | 0.87 | 0.85 |
| | $T_{qf}$ | 0.98 | 0.96 | | 0.94 | 0.89 |

FIGURE 7

| Best-fit value | | Constant Flow | | Constant Pressure | |
|---|---|---|---|---|---|
| | | $T_{pg}$ | $T_{pf}$ | $T_{qg}$ | $T_{qf}$ |
| 350 sec$^{-1}$ | $T0$ | 8.1 | 12.23 | 6.19 | 7.35 |
| | $\tau$ | 1.76 | 2.06 | 2.78 | 2.98 |
| 1250 sec$^{-1}$ | $T0$ | 3.0 | 4.77 | 1.87 | 4.50 |
| | $\tau$ | 1.75 | 2.36 | 3.54 | 2.82 |

FIGURE 8

| Best-fit value | | Constant Flow | | Constant Pressure | |
|---|---|---|---|---|---|
| | | $T_{pg}$ | $T_{pf}$ | $T_{qg}$ | $T_{qf}$ |
| 0.25 U/ml | $Z0$ | 74.74 | 106.2 | 0.0057 | 0.058 |
| | $\omega$ | 0 | 0 | 1.516 | 1.053 |
| | $\varphi$ | 0.0068 | 0.0073 | 0.0034 | 0.0018 |
| 0.5 U/ml | $Z0$ | 98.90 | 96.96 | 0.0043 | 0.0018 |
| | $\omega$ | 0 | 0 | 1.628 | 1.889 |
| | $\varphi$ | 0.0049 | 0.0022 | 0.0036 | 0.004 |

FIGURE 9

MICROFLUIDIC DEVICE FOR REAL-TIME CLINICAL MONITORING AND QUANTITATIVE ASSESSMENT OF WHOLE BLOOD COAGULATION

CROSS-REFERENCE TO RELATED APPLICATIONS

This application is a U.S. National Stage of International Patent Application No. PCT/US2014/060956, filed on Oct. 16, 2014, which claims the benefit of and priority to U.S. Provisional Patent Application No. 61/891,732, filed Oct. 16, 2013, the contents of which are each incorporated herein by reference in its entirety.

STATEMENT REGARDING FEDERALLY SPONSORED RESEARCH

Some aspects of the present disclosure were made with government support, under Grant No. N66001-11-1-4180 and HR0011-13-C-0025 awarded by the Defense Advanced Research Projects Agency (DARPA), and the government shares rights to such aspects of the present disclosure.

FIELD OF THE INVENTION

The present invention relates generally to microfluidic diagnostic devices, systems and methods and, more particularly, to a microfluidic diagnostic devices, systems and methods for real-time assessment of whole blood coagulation.

BACKGROUND OF THE INVENTION

Prevention of thrombosis with anticoagulants, such as heparin or coumadin, is critical for treatment of many diseases and conditions (e.g., atrial fibrillation, sepsis, trauma, prosthetic heart valves, various coagulapathies or other bleeding disorders) as well as for many life-saving procedures, including dialysis, hemofiltration, extracorporeal oxygenation (ECMO), angioplasty, intravenous fluid delivery, apheresis and collection of blood samples for analysis or culture. As thrombosis can result from activation of platelets as well as the coagulation cascade, anticoagulation therapy is typically supplemented by anti-platelet therapy. It would therefore be extremely helpful to be able to monitor global anticoagulation in real-time in the clinic because coagulation responses to variations in anticoagulant levels and platelet numbers can vary significantly among patients and in the same patient at different times. However, it is currently difficult to quickly and quantitatively ascertain the degree and efficiency of whole blood anti-coagulation and anti-platelet therapies, and there is no reliable method to do it rapidly at the bedside, having the possibility of using native blood.

Patients who have bleeding or clotting problems are now routinely monitored using Prothrombin Time (PT) and Activated Clotting Time (ACT)/Activated Partial Clotting Time (APTT) tests, which provide semi-quantitative measures of the extrinsic or intrinsic coagulation pathways respectively. However, the results produced by these assays can vary considerably depending on sample preparation, anticoagulation tubes, addition of activators, equipment, and user expertise. As a result, measurements of the same sample carried out at different sites or on different days often produce different results. The specificity and sensitivity of these tests are also poor and often result in false positive or negative cases in the clinic. Moreover, PT, ACT and APTT assays do not provide information on platelet function and therefore, do not serve as global coagulation tests. Because of the limitations of conventional blood clotting time tests, new point-of-care monitoring systems, such as thromboelastography (TEG) and rotation thromboelastometry (ROTEM) devices, have started to be integrated into clinical laboratories. These devices are able to provide greater information about hemostasis because they measure the cumulative contribution of plasma, platelets, leukocytes and red blood cells to the clotting response. These tests, however, measure clotting characteristics under static conditions (no flow) and hence, they are limited in their clinical utility with respect to platelet and endothelial cell functions, which are highly sensitive to physical forces, including pressure and flow. For example, fluid shear stresses and gradients of shear stresses in blood have a major impact on platelet activation and thrombosis and thus, coagulation monitors that do not incorporate fluid dynamics fail to accurately assess blood coagulation physiology as it occurs in the vasculature of a living patient.

SUMMARY OF THE INVENTION

A coagulation monitoring technology that incorporates relevant hemodynamic mechanical cues (shear stress and gradients) and that can be carried out with minimal (or none) sample preparation or operator training, in vitro or ex vivo, and integrated with extracorporeal blood perfusion systems (e.g., dialysis, hemofiltration, ECMO) would greatly enhance hemostasis assessment and patient or subject care (e.g., human patient/subject, animal patient/subject) capabilities in the clinic or laboratory. The microfluidic devices, systems and methods disclosed herein present an opportunity to fill this clinical unmet need by developing physiologically relevant bedside or lab bench tests that can help to both unravel the dynamics of thrombosis and aid in quantitative analysis of clot formation under both physiological and pathological fluid shear stress conditions, with the possibility of attaching the device directly to the patient blood vessel.

By way of example, and as discussed in more detail below, one embodiment of at least some of the present concepts comprises a microfluidic device comprising polydimethylsiloxane (PDMS) in which a network of rectangular microchannels (75×200 μm) are defined, these microchannels being approximately equivalent in size to 125 μm diameter living arterioles (FIG. 1). This microfluidic device and system is suitable for clinical or point-of-care use (e.g., bedside-capable) and is configured to measure thrombotic potential and platelet aggregation of whole blood (e.g., human blood, animal blood) in real-time.

In accord with the present concepts, full occlusion of microchannels in the device due to clot formation can be, for example, dynamically measured while independently controlling the concentration of anticoagulant (e.g., unfractionated heparin) or applied wall shear stress and gradient of shear stress.

Contrary to current static coagulation assessment devices, which ignore that thrombosis of blood vessels in vivo depends on the way blood flow in the circulation is maintained (e.g., the human heart pumps blood such that a relatively constant flow rate is maintained in the arterial circulation, while nearly constant pressure is sustained in the venous circulation), at least some aspects of the disclosed coagulation monitoring microfluidic device are configured to deliver blood in a substantially constant flow mode of operation and/or substantially constant pressure mode of operation using either a syringe pump or a constant-pressure pump, respectively. The parameters of substantially constant flow or substantially constant pressure also can be varied independently, if desired.

In accord with at least some aspects of the present concepts, clotting within the microfluidic channel is characterized by recording the rise in pressure (when flow is substantially constant in a constant flow mode of operation) or drop in flow rate (when pressure is substantially constant in a constant pressure mode of operation) and, using experimentally-validated phenomenological mathematical models described herein, develop one or more patient-specific or subject-specific predictive models for the temporal dynamics of whole blood clotting. The characteristic time constants of these respective models represent the clotting times of blood under shear flow. As these time constants are patient-specific or subject-specific, they can be determined by clinicians as a routine diagnostic test to quantitate, monitor, and track thrombogenicity, platelet function, bleeding disorders and anti-coagulation therapy under physiologically relevant conditions.

Current coagulation monitoring instruments have high variability, and often report unreliable and non-physiological clotting times. The present inventors have determined that the accuracy of these current coagulation monitoring instruments is low because they fail to measure contributions of blood rheology and hydrodynamic shear stresses and their gradients to hemostasis and thrombosis, which can vary from patient-to-patient and even day-to-day. Accordingly, the present concepts concern microfluidic devices, systems and methods that incorporate relevant flow hemodynamics and provide a quantitative measure of clotting activity that can significantly improve clinical assessment of blood coagulation, and which can be advantageously integrated with other systems, such as an extracorporeal blood perfusion devices.

In accord with one aspect of the present concepts, a microfluidic coagulation device, comprises at least one defining a plurality of microchannels, a first port at a first end portion of the substrate, the first port connecting to inlet ends of the plurality of microchannels, and a second port at a second end portion of the substrate, the second port connecting to outlet ends of the plurality of microchannels. An instrument that causes differential pressure or flow rate/shear across the first port is provided to drive a blood sample across the plurality of microchannels at a substantially constant flow rate. A first sensing device is configured to determine a pressure value in, or relating to, a pressure across the plurality of microchannels and a timer is provided to measure time. Further, a controller, which may comprise one or more processors which may be local and/or remote, is configured to determine, in combination with the first sensing device and the timer, a first pressure value at an initiation of flow, a first time at which a second pressure value is determined to be about twice the determined first pressure value, and a second time at which a third pressure value is about (1+e) times the determined first pressure value, and further configured to establish a patient coagulation model predictive of channel occlusion in accord with the relation $$\frac{\Delta P(t)}{\Delta P(0)} = 1 + e^{\frac{t-T_{pg}}{T_{pf}-T_{pg}}}$$

wherein $T_{pf}$ is the second time and $T_{pg}$ is the first time.

In another aspect of the present concepts, a microfluidic coagulation device, comprises at least one substrate defining a plurality of microchannels, a first port at a first end portion of the substrate, the first port connecting to inlet ends of the plurality of microchannels, and a second port at a second end portion of the substrate, the second port connecting to outlet ends of the plurality of microchannels. An instrument to apply a differential pressure across the first port is attached to the first port to apply a differential pressure across the first port to drive a blood sample across the plurality of microchannels. A first sensing device is configured to determine a flow rate in, or relating to, the plurality of microchannels and a timer is provided to measure time. A controller, which may comprise one or more processors which may be local and/or remote, is configured to determine, in combination with the first sensing device and the timer, (i) a first flow rate value at a first time corresponding to an initiation of flow, (ii) a second time at which a second flow rate value is determined to be about half the determined first flow rate value, (iii) a third time at which a third flow rate value is determined to be about (1+e) times lesser than the determined first flow rate value, and (iv) a patient coagulation model predictive of channel occlusion governed by the relation $$\frac{Q(t)}{Q(0)} = \frac{1}{1 + e^{\frac{t-T_{qg}}{T_{qf}-T_{qg}}}}$$

wherein $T_{qf}$ is the third time and $T_{qg}$ is the second time.

In yet another aspect of the present concepts, a method of assessing coagulation of a subject's blood comprises the acts of driving a blood sample from the subject at a substantially constant flow rate through a plurality of microchannels formed in a microfluidic device substrate and measuring a pressure, or a variable correlated with pressure, in at least one of the plurality of microchannels while the blood sample is moved through the plurality of microchannels at the substantially constant flow rate. The method also includes the acts of determining a first pressure value at an initiation of flow, determining a first time at which a second pressure value is determined to be about twice the determined first pressure value, and determining a second time at which a third pressure value is determined to be about (1+e) times the determined first pressure value. The method further includes the act of establishing a subject-specific coagulation model predictive of channel occlusion for the subject using the first time and the second time in the relation $$\frac{\Delta P(t)}{\Delta P(0)} = 1 + e^{\frac{t-T_{pg}}{T_{pf}-T_{pg}}}$$

wherein $T_{pf}$ is the second time and $T_{pg}$ is the first time. The method further includes the act of recording, on a physical storage medium, the established subject-specific coagulation model.

In yet another aspect of the present concepts, a method of assessing coagulation of a subject's blood comprises the acts of driving a subject's blood sample at a substantially constant pressure through a plurality of microchannels formed in a microfluidic device substrate and measuring a flow rate, or a variable correlated with flow rate, in at least one of the plurality of microchannels while the blood sample is moved through the plurality of microchannels at the substantially constant pressure. The method further includes the acts of determining a first flow rate value at an initiation of flow, determining a first time at which a second flow rate value is determined to be about half the determined first flow rate value, determining a second time at which a third flow rate value is determined to be about (1+e) times lesser than the determined first flow rate value, and establishing a subject-specific coagulation model predictive of channel occlusion for the subject using the first time and the second time in the relation $$\frac{Q(t)}{Q(0)} = \frac{1}{1+e^{\frac{t-T_{qg}}{T_{qf}-T_{qg}}}}$$

wherein $T_{qf}$ is the second time and $T_{qg}$ is the first time. The method also includes the act of recording, on a physical storage medium, the established subject-specific coagulation model.

In yet another aspect of the present concepts, a method of assessing coagulation of a subject's blood comprises the acts of driving a first blood sample for the subject at a substantially constant flow rate through a first plurality of microchannels formed in a first microfluidic device substrate and measuring a pressure, or a variable correlated with pressure, in at least one of the first plurality of microchannels while the first blood sample is moved through the first plurality of microchannels at the substantially constant flow rate. The method also includes the acts of determining a first pressure value at an initiation of flow, determining a first time at which a second pressure value is determined to be about twice the determined first pressure value, and determining a second time at which a third pressure value is determined to be about (1+e) times the determined first pressure value. The method further includes the act of establishing a first subject coagulation model predictive of channel occlusion using the first time and the second time in the relation:

$$\frac{\Delta P(t)}{\Delta P(0)} = 1 + e^{\frac{t-T_{pg}}{T_{pf}-T_{pg}}}$$

wherein $T_{pf}$ is the second time and $T_{pg}$ is the first time. The method further includes recording, on a physical storage medium, the established first subject-specific coagulation model. Still further, the method includes driving a second blood sample for the subject at a substantially constant pressure through a plurality of second microchannel formed in the first microfluidic device substrate or in a second microfluidic device substrate and measuring a flow rate, or a variable correlated with flow rate, in at least one of the plurality of second microchannels while the blood sample is moved through the plurality of second microchannels at the substantially constant pressure. The method further includes determining a first flow rate value at an initiation of flow, determining a first time at which a second flow rate value is determined to be about half the determined first flow rate value, determining a second time at which a third flow rate value is determined to be about (1+e) times lesser than the determined first flow rate value, and establishing a second subject-specific coagulation model predictive of channel occlusion using the first time and the second time in the relation $$\frac{Q(t)}{Q(0)} = \frac{1}{1+e^{\frac{t-T_{qg}}{T_{qf}-T_{qg}}}}$$

wherein $T_{qf}$ is the second time and $T_{qg}$ is the first time. The method further includes recording, on the physical storage medium, the established second subject-specific coagulation model.

In yet another aspect of the present concepts, a method of assessing coagulation of a subject's blood, comprises the acts of driving a blood sample at a substantially constant flow rate through a plurality of microchannels formed in a microfluidic device substrate and measuring a pressure, or a variable correlated with pressure, in at least one of the plurality of microchannels while the blood sample is moved through the plurality of microchannels at the substantially constant flow rate. The method further includes the acts of determining a first pressure value at an initiation of flow, determining a first time at which a second pressure value is determined to be about twice the determined first pressure value, and determining a second time at which a third pressure value is determined to be about (1+e) times the determined first pressure value. The method also includes the act of establishing a subject coagulation model predictive of channel occlusion and recording, on a physical storage medium, clotting times, utilizing the relation $$(T_{pg}, T_{pf}) = A_{(T_{pg},T_{pf})} e^{B_{(T_{pg},T_{pf})} C_{uh} - C_{(T_{pg},T_{pf})}^{\gamma}}$$

wherein A, B and C are subject specific variables relating to blood properties empirically determined by curve fitting the following relation $$\frac{\Delta P(t)}{\Delta P(0)} = 1 + e^{\frac{t-T_{pg}}{T_{pf}-T_{pg}}}$$

and wherein $T_{pf}$ is the second time and $T_{pg}$ is the first time.

In yet another aspect of the present concepts, a method of assessing coagulation of a subject's blood comprises the acts of driving a blood sample at a substantially constant pressure through a plurality of microchannels formed in a microfluidic device substrate and measuring a flow rate, or a variable correlated with flow rate, in at least one of the plurality of microchannels while the blood sample is moved through the plurality of microchannels at the substantially constant pressure. The method also includes the acts of determining a first flow rate value at an initiation of flow, determining a first time at which a second flow rate value is determined to be about half the determined first flow rate value, and determining a second time at which a third flow rate value is determined to be about (1+e) times lesser than the determined first flow rate value. The method also includes the acts of recording, on a physical storage medium, clotting times utilizing the relation $$(T_{qg}, T_{qf}) = A_{(T_{qg},T_{qf})} \gamma^{\mu} e^{B_{(T_{qg},T_{qf})} C_{uh} - C_{(T_{qg},T_{qf})}^{\gamma}}$$

wherein A, B C and ω are subject specific variables relating to blood properties empirically determined by curve fitting the following relation $$\frac{Q(t)}{Q(0)} = \frac{1}{1 + e^{\frac{t-T_{qg}}{T_{qf}-T_{qg}}}}$$

and wherein $T_{pf}$ is the second time and $T_{pg}$ is the first time.

In yet another aspect of the present concepts, a method of assessing an effect of a modifier on blood coagulation includes the acts of driving a first portion of a blood sample at a substantially constant flow rate through a first plurality of microchannels formed in a microfluidic device substrate and measuring a pressure, or a variable correlated with pressure, in at least one of the first plurality of microchannels while the first portion of the blood sample is moved through the first plurality of microchannels at the substantially constant flow rate. The method further includes the acts of determining a first pressure value at an initiation of flow of the first portion of the blood sample and determining a first time at which a second pressure value of the first portion of the blood sample is determined to be about twice the determined first pressure value of the first portion of the blood sample. The method further includes the acts of determining a second time at which a third pressure value of the first portion of the blood sample is determined to be about (1+e) times the determined first pressure value of the first portion of the blood sample and establishing a coagulation model predictive of channel occlusion for the first portion of the blood sample using the first time and the second time, for the first portion of the blood sample, in the relation $$\frac{\Delta P(t)}{\Delta P(0)} = 1 + e^{\frac{t-T_{pg}}{T_{pf}-T_{pg}}}$$

wherein $T_{pf}$ is the second time and $T_{pg}$ is the first time. The method further includes the acts of driving a second portion of the blood sample at a substantially constant flow rate through a second plurality of microchannels formed in the microfluidic device substrate or another microfluidic device substrate and adding a modifier to one of the second portion of the blood sample or the second plurality of microchannels. The method further includes the acts of measuring a pressure, or a variable correlated with pressure, in at least one of the second plurality of microchannels while the second portion of the blood sample is moved through the second plurality of microchannels at the substantially constant flow rate, determining a first pressure value at an initiation of flow of the second portion of the blood sample, and determining a first time at which a second pressure value of the second portion of the blood sample is determined to be about twice the determined first pressure value of the second portion of the blood sample. The method further includes the acts of determining a second time at which a third pressure value of the second portion of the blood sample is determined to be about (1+e) times the determined first pressure value of the second portion of the blood sample and establishing a coagulation model predictive of channel occlusion for the second portion of the blood sample using the first time and the second time, for the second portion of the blood sample, in the relation $$\frac{\Delta P(t)}{\Delta P(0)} = 1 + e^{\frac{t-T_{pg}}{T_{pf}-T_{pg}}}$$

wherein $T_{pf}$ is the second time and $T_{pg}$ is the first time. The method further includes the acts of comparing the coagulation model predictive of channel occlusion for the first portion of the blood sample to the coagulation model predictive of channel occlusion for the second portion of the blood sample to determine an effect of the modifier.

In another aspect of the present concepts, a method of assessing an effect of a modifier on blood coagulation includes the acts of driving a first portion of a blood sample at a substantially constant pressure through a first plurality of microchannels formed in a microfluidic device substrate and measuring a flow rate, or a variable correlated with flow rate, in at least one of the first plurality of microchannels while the first portion of the blood sample is moved through the first plurality of microchannels at the substantially constant pressure. The method further includes the acts of determining a first flow rate value at an initiation of flow of the first portion of the blood sample, determining a first time at which a second flow rate value of the first portion of the blood sample is determined to be about twice the determined first flow rate value, and determining a second time at which a third flow rate value of the first portion of the blood sample is determined to be about (1+e) times the determined first flow rate value. The method further includes the act of establishing a first coagulation model predictive of channel occlusion for the first portion of the blood sample using the first time and the second time in the relation $$\frac{Q(t)}{Q(0)} = \frac{1}{1 + e^{\frac{t-T_{qg}}{T_{qf}-T_{qg}}}}$$

wherein $T_{qf}$ is the second time and $T_{qg}$ is the first time. The method further includes the act of driving a second portion of the blood sample at a substantially constant pressure through a second plurality of microchannels formed in the microfluidic device substrate or another microfluidic device substrate and adding a modifier to one of the second portion of the blood sample or the second plurality of microchannels. The method further includes the acts of measuring a flow rate, or a variable correlated with flow rate, in at least one of the second plurality of microchannels while the second portion of the blood sample is moved through the second plurality of microchannels at the substantially constant pressure and determining a first flow rate value at an initiation of flow of the second portion of the blood sample. The method further includes the acts of determining a first time at which a second flow rate value of the second portion of the blood sample is determined to be about twice the determined first flow rate value of the second portion of the blood sample and determining a second time at which a third flow rate value of the second portion of the blood sample is determined to be about (1+e) times the determined first flow rate value of the second portion of the blood sample. The method further includes the act of establishing a second coagulation model predictive of channel occlusion for the second portion of the blood sample using the first time and the second time, for the second portion of the blood sample, in the relation $$\frac{Q(t)}{Q(0)} = \frac{1}{1+e^{\frac{t-T_{qg}}{T_{qf}-T_{qg}}}}$$

wherein $T_{qf}$ is the second time and $T_{qg}$ is the first time. The method further includes the act of comparing the coagulation model predictive of channel occlusion for the first portion of the blood sample to the coagulation model predictive of channel occlusion for the second portion of the blood sample to determine an effect of the modifier.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 6 is a table showing a Goodness of Fit parameter, $R^2$, of respective curve fits from derived mathematical relations for clotting dynamics, Eq. (1) and Eq. (2), at various shear rates and heparin concentrations for both infusion and pressure mode of device operation in accord with at least some aspects of the present concepts.

FIG. 7 is a table showing a Goodness of Fit parameter, $R^2$, of respective curve fits from derived mathematical relations for clotting times, at various shear rates and heparin concentrations for both infusion and pressure mode of device operation in accord with at least some aspects of the present concepts.

FIG. 8 is a table showing mean best-fit values of parameters of the mathematical model for clotting time vs. heparin concentration in accord with at least some aspects of the present concepts.

FIG. 9 is a table showing mean best-fit values of parameters of the mathematical model for clotting time vs. shear rate in accord with at least some aspects of the present concepts.

Figure 1:
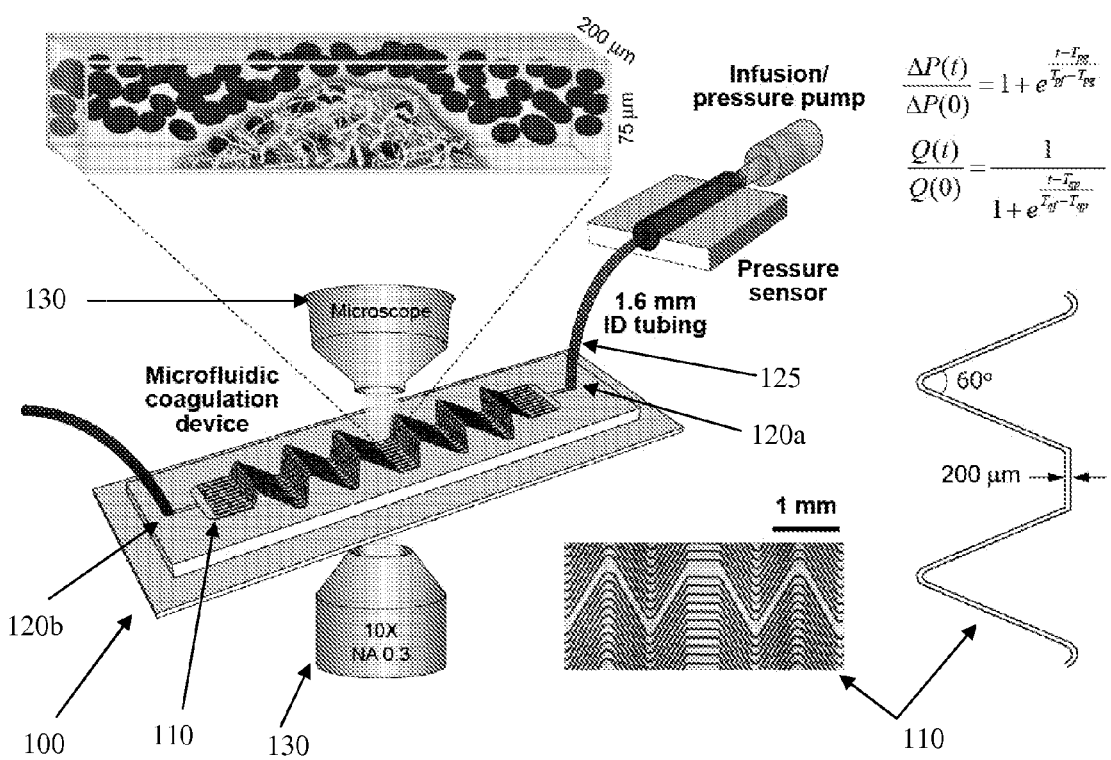
FIG. 1 shows a representation of microfluidic coagulation device in accord with at least some aspects of the present concepts.

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

DETAILED DESCRIPTION OF THE INVENTION

As discussed herein, the inventors found that clotting dynamics were sigmoidal and, based on this observation, the inventors developed and experimentally validated phenomenological mathematical models that accurately predict the temporal dynamics of whole blood clotting for both injection modes when either anticoagulant (heparin) concentration or applied shear rate is varied. The developed models reveal two clotting times: one indicates when clotting initiates, and the other determines when full vascular occlusion is produced. These models also incorporate the biophysical effects of fibrinogen diffusive transport and platelet aggregation. The inventors demonstrated, further, that the microfluidic device can, for example, be integrated with automated fluorescence imaging to enable simultaneous quantitation of coagulation and platelet aggregation. Accordingly, the multifunctional coagulation analysis system described herein is able to provide a quantitative standard for monitoring coagulation in a patient or subject (e.g., animal or human), either at the bedside or in a laboratory.

Described herein, in one embodiment of the present concepts, is a microfluidic device 100, shown by way of example in FIG. 1, containing a plurality of parallel microchannels 110 that mimic 125 μm diameter blood vessels and permit real-time analysis of clotting dynamics when a small volume (2-5 mL) of whole human blood is infused under either constant flow or constant pressure. The microfluidic device 100 used to obtain the data described herein comprises 12 parallel lanes of 200 μm wide and 75 μm high channels that repeatedly turn 60° over a length of 50 mm, as shown in FIG. 1, to provide a high hydrodynamic resistance, but retain laminar flow.

As discussed below, in the test configuration, 2-5 ml of human whole blood was pumped through an infusion or pressure pump followed by an inline pressure sensor that connected to ports 120a, 120b of the microfluidic device 100 via appropriate medical grade tubing (e.g., 1.6 mm ID). In infusion mode, clot formation leads to an increase in pressure, whereas in constant pressure mode, the flow rate drops with respect to time. In analyzing these results, phenomenological mathematical models and fit regression curves were applied to changes in pressure or flow, respectively. The characteristic constants of these models indicate clotting times at two stages—when the clot formation is accelerating and when the clot has completely occluded the channel. The clotting times are determined by the concentration of the anti-coagulant (e.g., heparin) and applied shear. Fluorescence microscopy of fibrinogen and platelets allow real-time monitoring of fibrin formation and platelet aggregation simultaneously.

In the testing conducted with the microfluidic device 100 of FIG. 1, fresh human blood stored in a 5 ml syringe (slip-tip Plastipak, BD, Franklin Lakes, N.J.) was pushed via syringe pump (PHD Ultra CP, Harvard Apparatus, Holliston, Mass.) through an inline, disposable pressure sensor (PREPS-N-000, PendoTECH, Princeton, N.J.) followed by the PDMS device within 15 minutes of blood draw. When flow rate was maintained to be constant, the syringe pump was operated in 'infusion' mode and the channel occlusion was measured by recording the rise in pressure over time using a data acquisition and analysis software (Winwedge Pro, TALtech, Philadelphia, Pa.). In the constant pressure operation mode, the syringe pump was used in 'pressure' mode that processes the feedback from a pressure sensor and modulates the motor speed and flow rate to maintain a set pressure. 2.5 inches and 6 inches of 3.2 mm OD, 1.58 mm ID medical grade tubing (Tygon S-50-HL, Saint Gobain Plastics, Merrimack, N.H.) were connected to the ports 120a, 120b of the device. As configured, one end of the inlet side tubing 125 is connected to the pressure sensor and the outlet side of the tubing is dipped in 3.8% sodium citrate. To further reduce clot formation inside the syringe, sensor and tubing, the blood-contacting surfaces were treated, if required, with slippery liquid-infused porous surface (SLIPS) technology, wherein low-pressure radio-frequency plasma exposure was used to activate the surfaces, followed by covalent coupling of an inert silane layer and addition of medical-grade liquid perfluorocarbon, used in blood substitutes. The syringe in the syringe pump was manually agitated every 2-3 minutes to prevent sedimentation of erythrocytes in the blood. Thrombus formation was observed using time-lapse imaging of an imaging device 130 of fluorescently-labeled fibrinogen (150 mg/ml, Alexa Fluor 488, Invitrogen, Grand Island, N.Y.). In the test setup, the imaging device 130 used was a fluorescence imaging configured Carl Zeiss Axio 3 Observer microscope (10×, NA 0.3 objective), but other imaging devices may be readily used in accord with the present concepts.

Platelets were isolated from whole blood by two centrifugations (200 g followed by 500 g) and labeled with calcein orange (2 µM, Invitrogen, Grand island, NY) for 10 minutes. Multiple fluorescent microscopic images were recorded from neighboring regions using automatic scanning and stitched together to form a large region panorama. The presence and size of large fluorescent platelet aggregates were then analyzed using automated image capture and an image analysis protocol. The heparin concentration and wall shear rate were varied independently in these experiments. The wall shear stress/rate was determined from analytical formulae derived for the rectangular microchannels 110.

The microfluidic device 100 (FIG. 1) used in the testing described herein comprises SU8 2075 (MicroChem. Corp., Newton, Mass.) master templates fabricated on Si wafers (University Wafer Corp., Boston, Mass.) using photolithography, and more particularly soft lithography of polydimethylsiloxane (PDMS). 27 Slygard 184 PDMS prepolymer (Dow Corning, Midland, Mich.) was cast on the silanized master, which had the positive relief of the channel features formed by the SU-8 photoresist. The PDMS was then cured at 60° C. in a convection oven for 120 minutes. The cured PDMS was peeled off the master and bonded to a 500 µm high PDMS coated glass slide after treating both with oxygen plasma (Plasma Etch, Carson City, Nev.). The microfluidic devices 100 was primed with perfluorodecalin (PFD, Sigma-Aldrich), a medically approved lubricant, before use.

After informed, written consent as per ethical guidelines of Institutional Review Board (IRB) of Partners Healthcare and Harvard University, blood samples were collected from non-smoking healthy volunteers in a standard 6 ml no-additive blood vacutainer (BD and Company, Franklin Lakes, N.J., USA) and 1000 U/ml unfractionated heparin was immediately added to a required concentration. Coagulation experiments were initiated within ~15 minutes after the blood draw. For experiments where heparin concentration was below 0.25 U/ml, blood was first drawn in 3.2% 5 ml sodium citrate vacutainers (BD and Company, Franklin Lakes, N.J., USA). Citrated blood (Research Blood Components, Brighton, Mass., USA) was also purchased for some studies, and the coagulation activity of these samples was restored by adding 75 µl/ml of 100 mM calcium chloride/75 mM magnesium chloride solution. Aspirin (Sigma Aldrich, St. Louis, Mo.) was dissolved in phosphate buffer solution (PBS) to a concentration of 20 mM and added to blood to reach a final concentration of 500 µM. Prasugrel (Sigma Aldrich, St. Louis, Mo.) was dissolved in dimethylsulfoxide (DMSO) at 1 mg/ml and added to blood to reach a final concentration of 25 µg/ml.

In the statistical analyses described herein, unless otherwise specifically mentioned, all data is presented as mean±SD. Two-tailed P values were obtained from the statistical t-test to compare the means. Data analysis and curve fitting was performed using Graphpad Prism V6 (Graphpad Software, San Diego, Calif.).

Figure 2A:
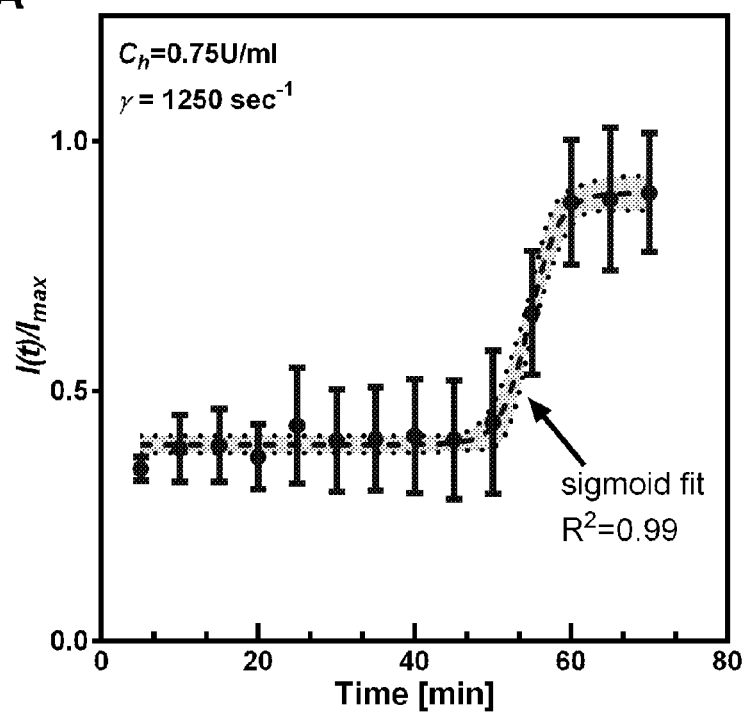
FIGS. 2A-2B show dynamics of thrombus formation using fluorescence timelapse microscopy of labeled fibrinogen, in accord with at least some aspects of the present concepts, utilizing the microfluidic coagulation device of FIG. 1.
Figure 2B:
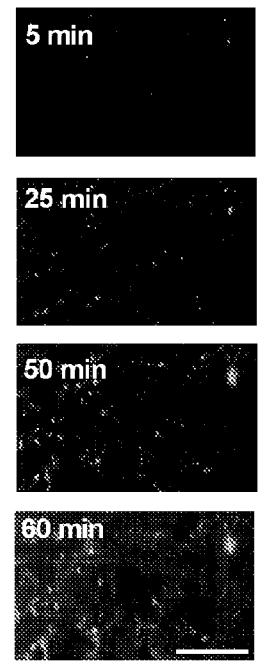

FIGS. 2A-2B show dynamics of thrombus formation using fluorescence timelapse microscopy of labeled fibrinogen, in accord with one aspect of the present concepts, utilizing the microfluidic coagulation device 100 of FIG. 1. In FIG. 2A, the fluorescence intensity normalized by the maximum, follows a sigmoidal trend over time in a microchannel 110, leading to its occlusion. The data can be fit using a three-parameter sigmoid equation. The dotted lines and shaded grey area show 95% confidence interval of the fitted curve. n=3, $R^2$=0.99. In FIG. 2B, stacked fluorescent micrographs of labeled fibrinogen at shown at four different time durations from timelapse imaging of fluorescent fibrinogen for whole blood flow containing 0.75 U/ml heparin anti-coagulant and an imposed shear rate of 1250 sec-1. Each figure is a scan of 4×1 tiles (10× objective) stitched together. The white scale bar at the bottom right of the bottom micrographs is 500 µm.

Figures 3A, 3B, 3C, 3D:
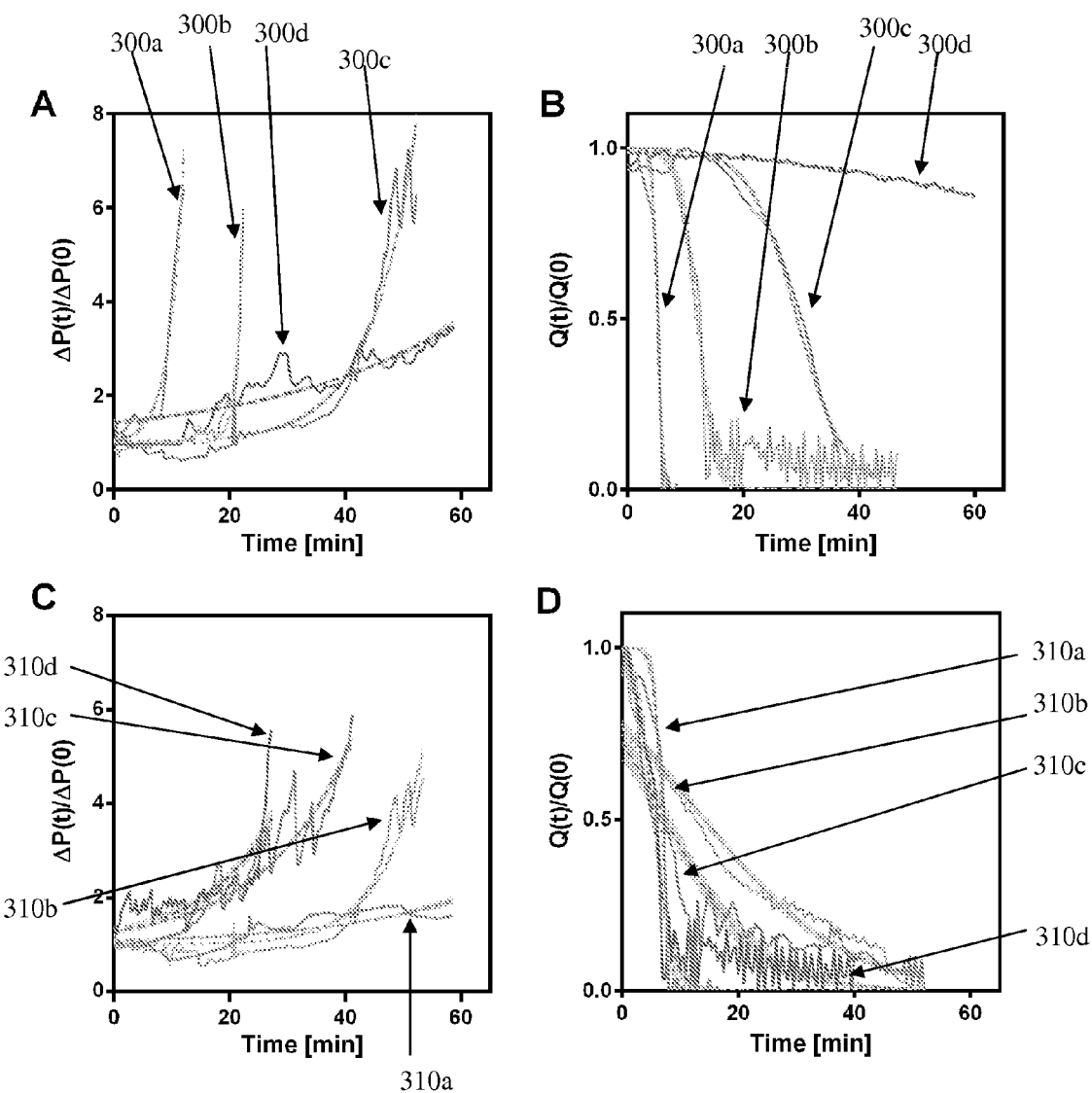
FIGS. 3A-3D show a quantitative assessment of whole blood coagulation in a microfluidic device in accord with FIG. 1 operated under infusion or pressure pump mode, in accord with at least some aspects of the present concepts.

FIGS. 3A-3D show a quantitative assessment of whole blood coagulation in a microfluidic device 100 in accord with FIG. 1 operated under infusion or pressure pump mode. By varying the heparin concentration at a given shear rate/stress of 350 sec$^{-1}$ (14 dynes/cm$^2$), in infusion mode, the pressure grows exponentially with time (FIG. 3A) and in pressure mode, the flow drops in sigmoidal fashion with time (FIG. 3B). In FIGS. 3A-3B, reference numeral 300a denotes a plot corresponding to a flow rate of 0 U/ml, reference numeral 300b denotes a plot corresponding to a flow rate of 0.25 U/ml, reference numeral 300c denotes a plot corresponding to a flow rate of 0.5 U/ml, and reference numeral 300d denotes a plot corresponding to a flow rate of 1 U/ml. Similarly, by varying the shear rate/stress at heparin concentration of 0.5 U/ml, in infusion mode, the pressure grows exponentially with time (FIG. 3C) and, in pressure mode, the flow drops in sigmoidal fashion with time (FIG. 3D). In FIGS. 3C-3D, reference numeral 310a denotes a plot corresponding to a flow rate of 150 sec$^{-1}$, reference numeral 310b denotes a plot corresponding to a flow rate of 350 sec$^{-1}$, reference numeral 310c denotes a plot corresponding to a flow rate of 750 sec$^{-1}$, and reference numeral 310d denotes a plot corresponding to a flow rate of 1500 sec$^{-1}$. The solid lines in FIGS. 3A-3D are measured quantities and the dotted lines represent a 95% confidence interval of regression curves fit with analytical model Eq. (1) and Eq. (2), described herein, respectively. The goodness of fit parameter $R^2$ is tabulated in FIG. 6.

Figures 4A, 4B, 4C, 4D:
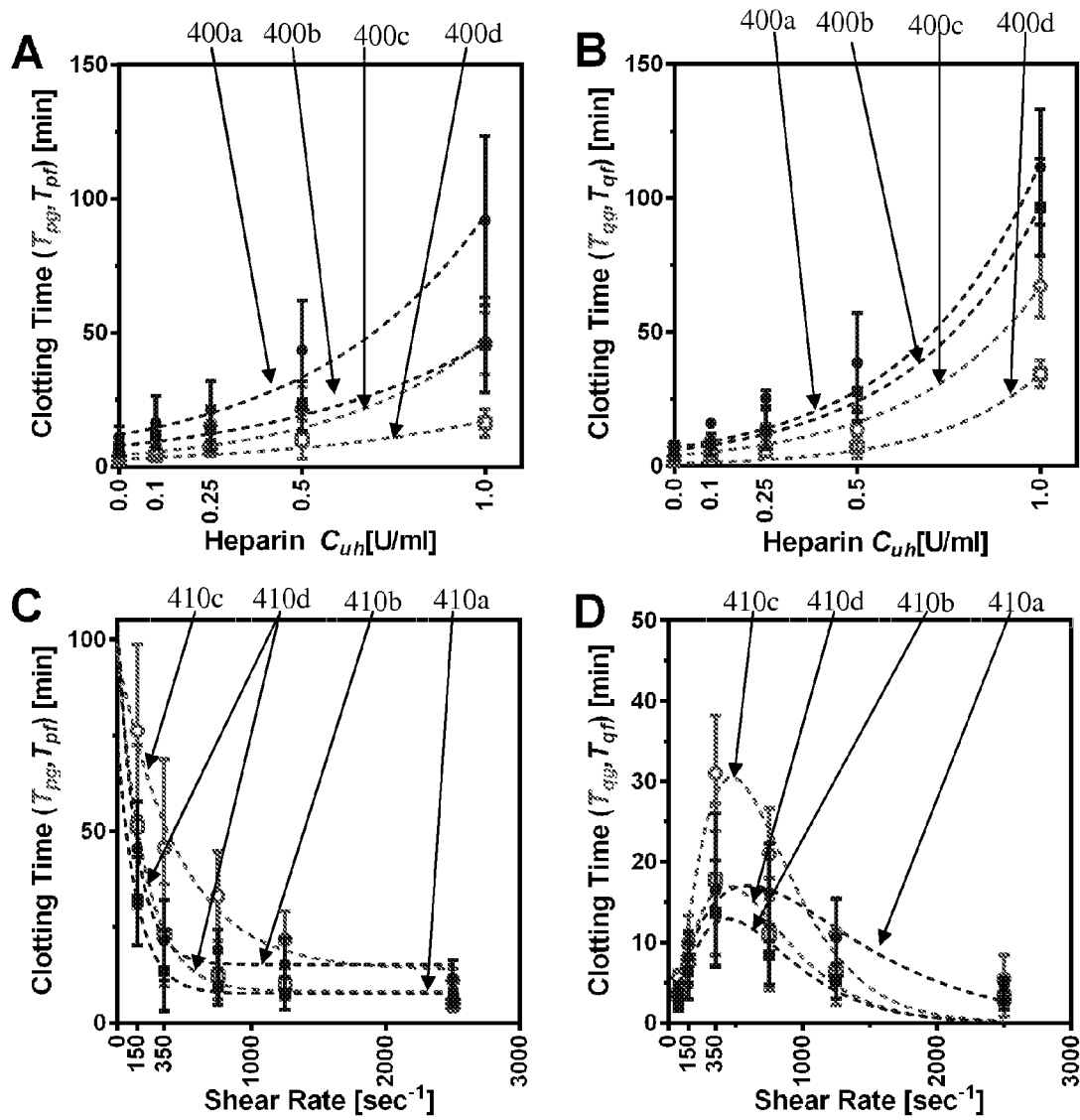
FIGS. 4A-4D show clotting times derived from the phenomenological analytical models as a function of unfractionated heparin concentration and shear rate, in accord with at least some aspects of the present concepts.

FIGS. 4A-4D show clotting times derived from the phenomenological analytical models as a function of unfractionated heparin concentration and shear rate, in accord with at least some aspects of the present concepts. By varying the heparin concentration in the range 0-1 U/ml and setting the shear rates 350 sec$^{-1}$ (14 dynes/cm$^2$) and 1250 sec$^{-1}$ (50 dynes/cm$^2$) respectively, in infusion mode (FIG. 4A), the clotting times, ($T_{pg}$ and $T_{pf}$), and in pressure mode (FIG. 4B), the clotting times, ($T_{qg}$ and $T_{qf}$), increase exponentially with heparin concentration. In FIGS. 4A-4B, reference numeral 400a denotes a plot corresponding to $T_{pg}$, $T_{qg}$ at 350 sec$^{-1}$, reference numeral 400b denotes a plot corresponding to $T_{pf}$, $T_{qf}$ at 350 sec$^{-1}$, reference numeral 400c denotes a plot corresponding to $T_{pg}$, $T_{qg}$ at 1250 sec$^{-1}$, and reference numeral 400d denotes a plot corresponding to $T_{pf}$, $T_{qf}$ at 1250 sec$^{-1}$. By varying the shear rates in the range 75-2500 sec$^{-1}$ (3-100 dynes/cm$^2$) and setting the heparin concentration 0.25 and 0.5 U/ml respectively, in infusion mode (FIG. 4C), the clotting time times, ($T_{pg}$ and $T_{pf}$), decay exponentially and in pressure mode (FIG. 4D), the clotting time times, ($T_{qg}$ and $T_{qf}$), follow the relation, Clot Time=$Z0\gamma^{\omega}e^{-\varphi\gamma}$, with shear rate/stress. In FIGS. 4C-4D, reference numeral 410a denotes a plot corresponding to $T_{pg}$, $T_{qg}$ at 0.25 U/ml, reference numeral 410b denotes a plot corresponding to $T_{pf}$, $T_{qf}$ at 0.25 U/ml, reference numeral 410c denotes a plot corresponding to $T_{pg}$, $T_{qg}$ at 0.5 U/ml, and reference numeral 410d denotes a plot corresponding to $T_{pf}$, $T_{qf}$ at 0.5 U/ml. The dotted lines are regression curves fitted to the analytical relationships respectively wherein n=3 experiments were conducted in each case and the $R^2$ goodness of fit parameter for each case is tabulated in FIG. 7.

Figures 5A, 5B, 5C:
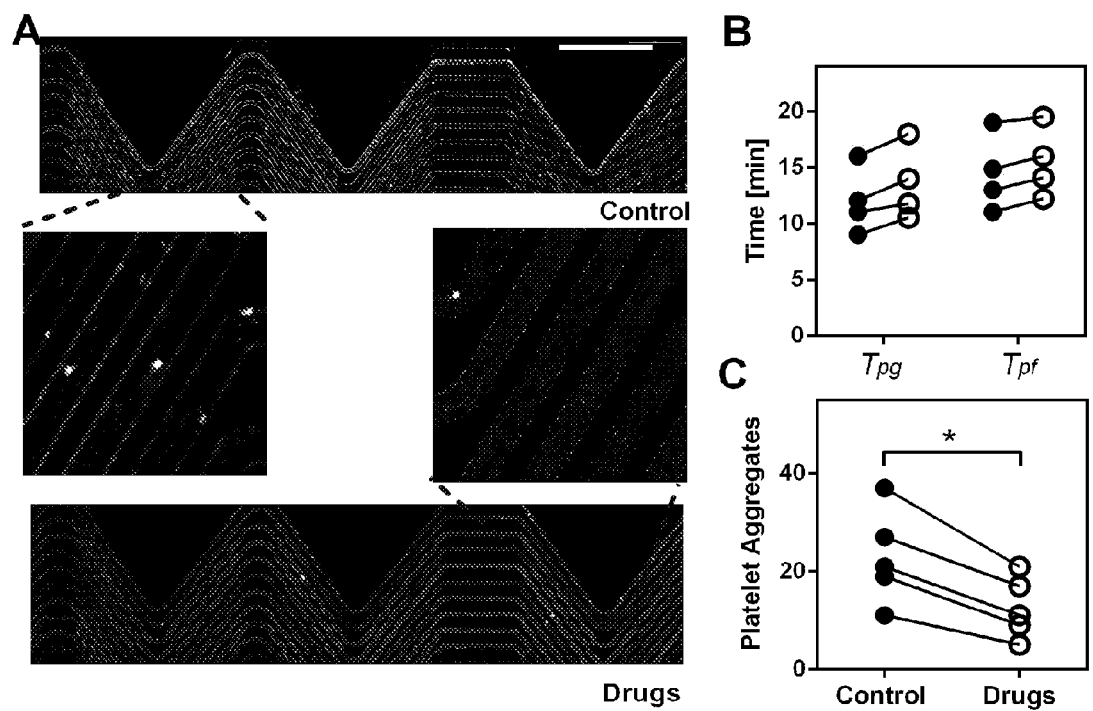
FIGS. 5A-5C show an analysis of platelet aggregation using the microfluidic coagulation measurement device in accord with at least some aspects of the present concepts.

FIGS. 5A-5C show an analysis of platelet aggregation using the microfluidic coagulation measurement device 100 in accord with at least some aspects of the present concepts. In FIG. 5A, fluorescent stacked images of the microfluidic device 100 show formation of aggregates of fluorescently-labeled platelets when whole human blood is flowed through the microfluidic device of FIG. 1 without (Control) or with 500 µM aspirin and 25 µg/ml prasugrel (Drugs). Images at the center of FIG. 5A are higher magnification insets of the upper and lower images. The scale bar (white at top right of top slide in FIG. 5) is 5 mm. FIG. 5B shows addition of the platelet inhibitor drug combination (Drugs) increased the clotting time compared to Control when the device was operated at a constant shear rate of 1250 sec$^{-1}$ (n=4), wherein the solid circle represents the Control and the empty circle (right side of the line segments) represents the Drugs. In FIG. 5C, addition of the drug combination significantly decreased the number of platelet aggregates in the blood compared to control untreated samples (*P<0.05; n=5).

Figure 13A:
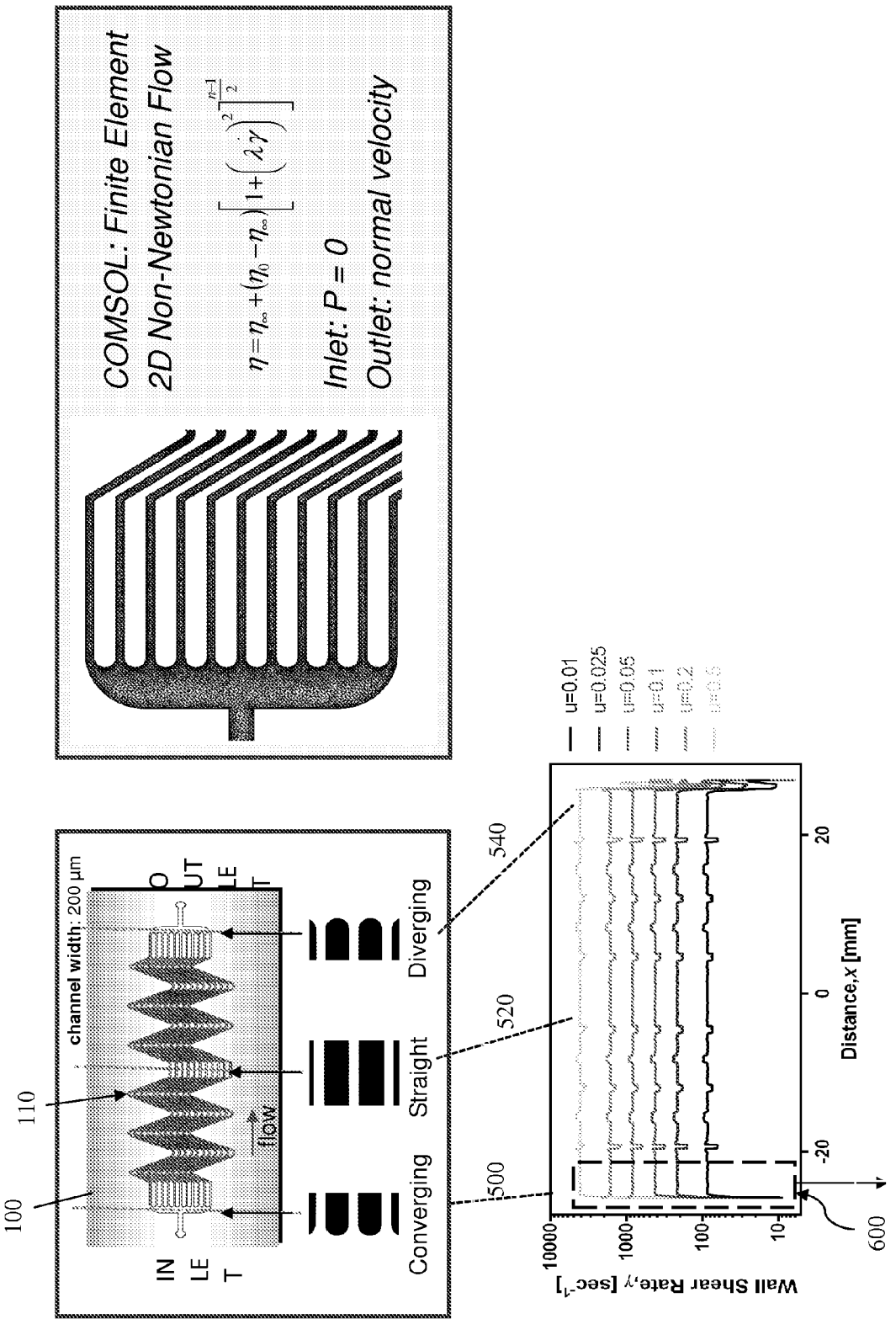
FIGS. 13A-13C shows computational modeling of blood flow in a biomimetic vascular network, showing shear rate and shear rate gradients therein, in accord with at least some aspects of the present concepts.
Figure 14:
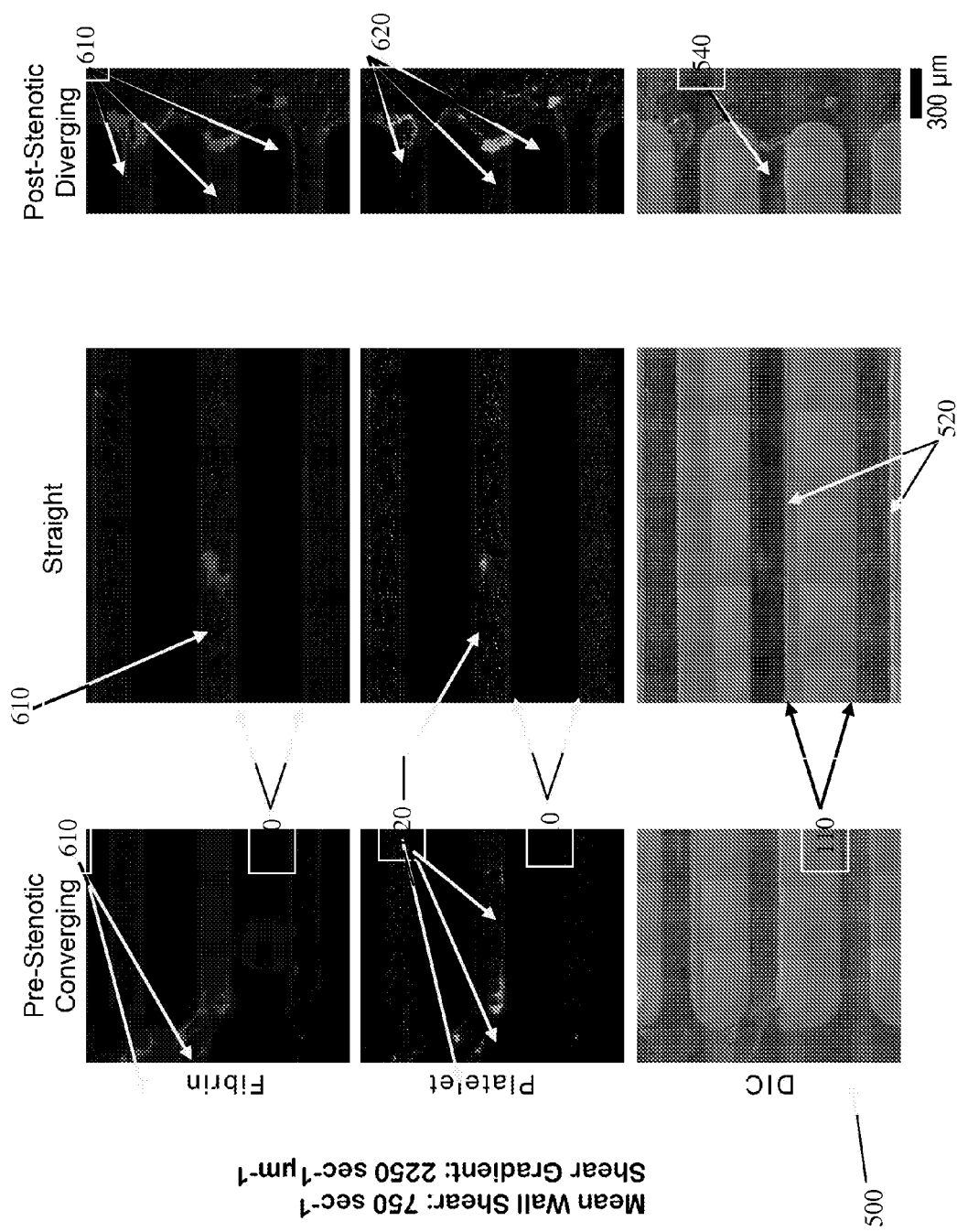
FIG. 14 shows the effect of shear and shear gradient on fibrin and platelet adhesion, wherein it is shown that fibrin and platelet adhesion is maximum at post-stenotic/diverging section of the microfluidic device represented in FIGS. 13A-13C.

The microfluidic coagulation device 100 was designed to operate at shear rates ranging from about 75 sec$^{-1}$ to 2500 sec$^{-1}$ (3 to 100 dynes/cm$^2$) in such a way that the corresponding flow rates can be maintained within the range of about 5-150 µl/min. Desirably, a shear rate is maintained to be substantially constant, so as not to vary more than a predetermined amount from the set shear rate (e.g., within 10% from a set value, and still more preferably within about 5% from the set value, and still more preferably within 2% from the set value). Flow rates outside of the above-noted range, for the particular microfluidic coagulation device 100 utilized, were found to be undesirable as they would result in frequent red blood cell sedimentation or require large volume of human donor blood respectively. However, different microchannels 110 configurations (e.g., different cross-sectional area) and/or different clinical parameters (e.g., a larger volume of patient blood) could certainly warrant flow rates outside of the above-specified range in order to operate at shear rates ranging from about 75 sec$^{-1}$ to 5000 sec$^{-1}$ (3 to 200 dynes/cm$^2$). By way of example, microchannel 110 configurations in the microfluidic devices 100 of FIG. 13A and FIG. 14 provide a geometry that allows the fluid to pass through a converging zone 500 (flow acceleration; prestenosis) into multiple lanes made of microchannels of substantially constant cross-sectional area 520 having curved sections and straight sections. The fluid then exits through a diverging section 540 (flow deceleration; post-stenosis) into a common outlet. The straight section microchannels 110 of the microfluidic device 100 were sized to enable real-time optical microscopic imaging using a low magnification (10×; 0.3 N.A.) objective. For these practical reasons, the microfluidic device 100 of FIG. 1 comprises 12 parallel microchannels 110 that are each approximately 200 µm wide and 75 µm high. The rectangular cross-sectional surface area of the microchannels 110 was equivalent to a 125 µm diameter circular arteriole. To acquire a good signal-to-noise ratio from the pressure sensor utilized in the set-up of FIG. 1, the channel length was optimized for the highest possible hydrodynamic resistance, while restricting the overall length of the microfluidic device 100 so that it fits on a standard glass microscope slide (50 mm×75 mm). This was achieved by incorporating a continuous series of 60° bends in the channels, except a straight 1 cm section at the center of the device where optical imaging is performed (FIG. 1). The particular curvilinear structure of the microchannels 110 was designed, given the arbitrary geometric constraint of utilizing a standard glass slide, to achieve the best signal-to-noise ratio out of the sensor used (e.g., the pressure sensor used to measure pressure), that is, it can measure smaller changes in hydraulic resistance. If a more expensive, or more highly-sensitive, pressure sensor were used, for example, the design-envelope for the microchannels 110 changes, permitting different geometries (e.g., straight) to be used with a suitable signal-to-noise ratio.

Absent the mere preference to size the microfluidic device 100 to fit on a standard glass microscope slide, desired constraints of low Reynolds number flow and a high signal-to-noise ratio (e.g., imposing a minimum dimension of the microchannels of about 15 µm and a maximum dimension of about 1.5-2.0 mm), there is no limit on the sizing of the microfluidic device 100 and/or microchannels 110. Thus, the microfluidic device 100 may be dimensionally larger or smaller than that described herein and, further, the number or microchannels 110 and/or microchannel configurations may be freely varied (e.g., the microchannels 110 may be straight, may be defined by a 3-D geometry, etc.). Further, although not shown, one or more of the microchannels 110 may optionally comprise one or more additional microchannel inlets permitting the any of the one or more microchannels to have additional fluid(s) introduced therein, such as a drug to be mixed in with the flow in the microchannel). Moreover, it is to be emphasized that the depicted microfluidic device 100 was designed in support of the testing and analysis described herein and the utilization of microscopy or imaging devices (e.g., 130, FIG. 1) is not a necessary aspect of the microfluidic device-based coagulation system described herein. Due to the relationships derived by the present inventors, described herein, the dynamics of coagulation are determinable solely by measurement of pressure or flow rate. Accordingly, whereas the disclosed microfluidic device 100 of FIG. 1 comprises a transparent substrate to facilitate imaging of the coagulation, an opaque substrate alternatively may be used. Only if platelet aggregration is simultaneously measured, microscopy is needed.

The dynamics of fibrin clot formation in a blood vessel in vivo, or in an in vitro hollow channel, consist of three stages—a steady reaction time, a growth phase, and saturation (full stenosis)—resulting in a sigmoid curve. To validate the sigmoidal dynamics of clot formation in the microfluidic device 100 of FIG. 1, comprising rectangular channels, time-lapse microscopic analysis of whole human blood spiked with fluorescently-labeled fibrinogen and an intermediate level therapeutic dose (0.75 U/mL) of heparin anticoagulant was performed while imposing a shear rate of 1250 sec$^{-1}$ (50 dynes/cm$^2$) in constant flow mode. When the mean fluorescence intensity, I(t), normalized by the intensity of a fully clotted region ($I_{max}$) was plotted against time, the inventors determined that, at a fixed site within the linear portion of the microfluidic channel, clotting followed a sigmoidal trend indicative of the three stages of clot formation (FIG. 2A,B).

Previous studies have shown that the size of a growing thrombus measured in vitro correlates linearly with measured light intensity. Therefore, it was assumed that, in the microfluidic device 100, $I(t)/I_{max} \approx A_{max}/A(t)$, where A(t) is the cross-sectional area available for blood flow through the occluding channel at a given time, and $A_{max}$ is the initial cross-sectional area of the microchannel 110.

The hydraulic resistance ($R_h$) of the occluding microchannel 110 approximately scales as $$R_h(t) \cong \frac{1}{A(t)^2}.$$

Because the microfluidic device 100 of FIG. 1 has parallel microchannels 110 and each microchannel will not occlude equally at the same time, the hydraulic resistance of the whole device scales as $$R_h(t) \cong \frac{1}{A(t)^k},$$

k≤2.

For simplicity, it is assumed that k is unity, which leads to the conclusion that $R_h(t)$ of an occluding microchannel 110 follows a simple sigmoid. Based on the Hagen-Poiseuille law ($Q = \Delta P/R_h$) of laminar flow, where Q is flow rate and ΔP is pressure-drop, when constant flow is applied with a standard syringe pump using the infusion mode of operation (Q=constant), the present inventors proposed the following model to predict clotting times and clotting dynamics (e.g., channel occlusion) where ΔP increase follows the following relation (FIG. S1):

$$\frac{\Delta P(t)}{\Delta P(0)} = 1 + e^{\frac{t - T_{pg}}{T_{pf} - T_{pg}}}; Q(t) = Q(0) \tag{1}$$

where $T_{pg}$ and $T_{pf}$ are the characteristic parameters of the fitted exponential growth curve that represent time for the pressure to double and (1+e) times its initial value, respectively. Physiologically, these times represent the growth and saturation phases of clotting under constant flow, respectively, which is analogous to development of hypertensive pressures in an arterial vessel in vivo.

Alternatively, extending the analytical model for predicting clotting times and clotting dynamics to blood injection with a pressure pump (ΔP=constant), the present inventors predicted that the drop in flow (Q) of an occluding channel follow the following relation of an inverted sigmoid (FIG. S1):

$$\frac{Q(t)}{Q(0)} = \frac{1}{1 + e^{\frac{t - T_{qg}}{T_{qf} - T_{qg}}}}; \Delta P(t) = \Delta P(0) \tag{2}$$

wherein $T_{qg}$ and $T_{qf}$ are the characteristic parameters of the fitted sigmoidal decay curve that represent time for flow to reduce to half and (1+e) times its initial value, respectively. Physiologically, these times respectively represent the growth and saturation phases of clotting, which could lead to flow stasis as might occur, for example, in a blood vessel of the venous circulation in vivo.

Figure 11:
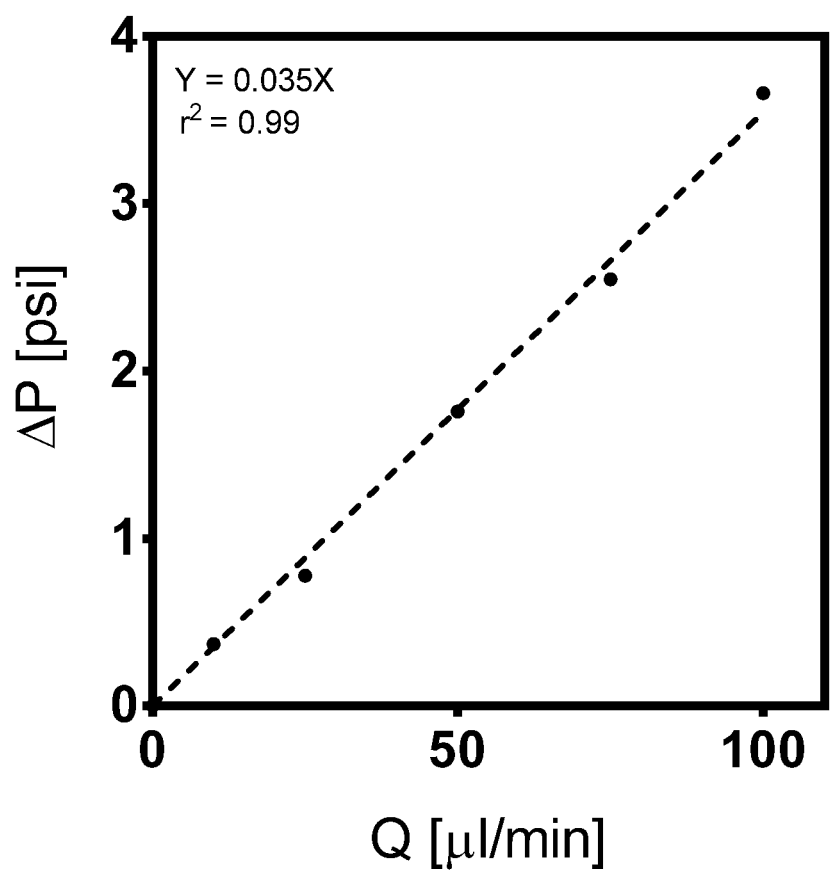
FIG. 11 shows whole blood, drawn in sodium citrate, perfused through the microfluidic device of FIG. 1, and $\Delta P$-$Q$ response curve is plotted to estimate $\Delta P(0)$ and $Q(0)$ in infusion mode and pressure mode of operation respectively in accord with at least some aspects of the present concepts.

To determine the initial values of the mathematical models, ΔP(0) and Q(0), the present inventors assumed that the physical parameters of the blood were constant at the beginning of coagulation monitoring, and therefore, can be obtained from the ΔP-Q calibration curve of citrated blood perfused through the device at different flow rates. The data obtained indeed revealed a linear relationship between the change in pressure and applied flow rate for laminar anticoagulated blood flow and therefore, the line of linear regression represents the ΔP-Q calibration curve (FIG. 11). The rise in pressure when the flow rate is constant (FIG. 3A) and decay in flow when the pressure is constant (FIG. 3B) were experimentally determined at different heparin concentrations at a constant physiological shear rate of 350 sec$^{-1}$ (14 dynes/cm$^2$) and it was found that the regression curves based on mathematical models (1) and (2) fit the data with a high level of accuracy (FIG. 6). Similarly, when the fluid shear stress at a constant heparin concentration (0.5 U/mL) was varied, it was found to fit the above analytical models to the experimental measurements for pressure rise at a constant flow rate (FIG. 3C) or flow decay at a constant pressure (FIG. 3D), with the curve fits being found to be extremely accurate (FIG. 6). The goodness of fit parameter ($R^2$) values shown in FIG. 6 from the entire regression curve fits also confirmed that the mathematical models are highly reliable. Therefore, the best-fit values of model parameters, that is, clotting times ($T_{pg}$ and $T_{pf}$; $T_{qg}$ and $T_{qf}$) represent the clotting dynamics of human whole blood in this biomimetic microfluidic device 100 for heparin concentrations in the range 0-1 U/ml and shear rate in the range 75-2500 sec$^{-1}$ (6-100 dyne/cm$^2$).

The inventors then set out to test the diagnostic and clinical utility of blood clotting times ($T_{pg}$ and $T_{pf}$ for infusion; $T_{qg}$ and $T_{qf}$ for pressure) determined from these regression models by validating their response to changes in unfractionated heparin concentration and applied shear, and comparing these results with those from known systems. The standard coagulation tests, including activated partial thromboplastin time (APTT) and activated clotting time (ACT), have shown an exponential relation between clotting time and the concentration of unfractionated heparin when tested at clinically relevant concentrations (0-1 U/mL). This relation can be described as, ClotTime=T0e$^{\tau C_k}$, where T0 is the clotting time for blood with no heparin and $\tau$ is the heparin sensitivity value. To validate this exponential relationship and evaluate the utility of microfluidic device 100 for analyzing anti-coagulation therapy in the clinic, heparin sensitivity in the relevant concentration range (0-1 U/mL) was measured and the characteristic clotting parameters, $T_{pg}$ and $T_{pf}$ (infusion mode) and $T_{qg}$ and $T_{qf}$ (pressure mode) were evaluated, as determined by fitting regression curves based on equations (1) and (2), respectively, for coagulating whole human blood flow in the microfluidic device 100, as described above. In the infusion mode, both $T_{pg}$ and $T_{pf}$ accurately exhibited exponential increases as the heparin concentration was raised from 0 to 1 U/mL at physiological (350 sec$^{-1}$; 14 dynes/cm$^2$) and pathological (1250 sec$^{-1}$; 50 dynes/cm$^2$) fluid shear levels as reported by the goodness of fitness parameter (FIG. 4A, FIG. 7). The exponential trend using the constant pressure mode was also validated. Both $T_{qg}$ and $T_{qf}$ increased exponentially as the heparin concentration was raised using the same two shear rates (FIG. 4B, FIG. 7), and in all cases, clotting times were reduced at high versus low shear (FIG. 4. A,B). In addition, the model predicts a clotting time of blood from a healthy patient with no-anticoagulant (T0) to be approximately 2-12 minutes, and the heparin sensitivity value ($\tau$) to be in the range of 1.75-3.5 (U/ml)$^{-1}$, which is consistent with typical values reported by the standard coagulation tests, shown in FIG. 8.

Current coagulation tests applied in the clinic do not incorporate the physiological contributions of hemodynamic shear stresses that result, for example, in increased clotting of veins at low shear stresses (relative to physiological) and in small arteries at high shear stresses. In addition, standard clotting time instruments report only one value of clotting time at stasis that could be inaccurate in patients undergoing procedures employing extra-corporeal circuits (e.g., ECMO, dialysis, hemofiltration) where blood flow is both variable and a critical determinant of coagulation. Thus, the present inventors set out, using microfluidic device 100, to develop and test a mathematical model to predict the clotting time when shear is varied. Clotting at low shear is governed by the diffusion-reaction transport of coagulation factors such as fibrinogen and therefore, a model of power-law kinetics ($\gamma^\omega$) was used, where $\omega$ is the power-law constant. Coagulation at high shear is dominated by platelet activation, the impact of which on blood clotting time was modeled using an exponential relationship (e$^{-\phi\gamma}$), where $\phi$ is the decay constant. For simplicity, mutual independence of fibrinogen diffusion and platelet aggregation was assumed, and the inventors developed a mathematical model of clotting time in which Clot Time=Z0$\gamma^\omega$e$^{-\phi\gamma}$, where Z0 is a model constant (the individual and coupled behavior of the power-law and exponential terms of this analytical model are shown in FIG. 8).

When blood clotting was measured using in the infusion mode, a decrease in clotting times ($T_{pg}$ and $T_{pf}$) was only observed when shear rates were increased from about 150 sec$^{-1}$ to about 2500 sec$^{-1}$ (about 6 to 100 dynes/cm$^2$)(FIG. 4C). In the infusion mode, when shear rate was reduced to 75 sec$^{-1}$, the blood did not clot, as no increase in pressure was observed during the 60 minute infusion time. Accordingly, for this combination of microfluidic device 100 (FIG. 1) and test conditions, the inventors were not able to fit the mathematical model accurately or extract clotting times. Because a drop in clotting time at the lowest shear rates that could be applied in the test configuration were not observed, the contribution of diffusive transport of coagulation enzymes proposed in the mathematical model appears to be negligible in this device at shear rates above 75 sec$^{-1}$. Thus, by assuming the power constant ($\omega\approx 0$), clotting times can be fit accurately with a more simple exponential decay relation: ClotTime=Z0e$^{-\phi\gamma}$ (FIGS. 7, 9).

However, when similar measurements were made in the constant pressure mode, the clotting times ($T_{qg}$ and $T_{qf}$) decreased at shear rates below 350 sec$^{-1}$ (14 dynes/cm$^2$) for two different heparin concentrations (0.25 U/ml and 0.5 U/ml; FIG. 4D). At shear above 350 sec$^{-1}$, an exponential decrease was observed and our mathematical model fit accurately with the power constant, $\omega>0$ (FIGS. 7, 9). Interestingly, the model also predicted that the maximum clotting time will occur at a shear rate between 200 to 500 sec$^{-1}$ (8-20 dynes/cm$^2$), which corresponds well to the physiological shear range expected for a small (~100 μm) blood vessel. These results suggest that when studied in the constant pressure mode of operation, blood clotting inside the microfluidic device 100 can be determined by diffusion of coagulation proteins at low shear. In addition, the model predicts that platelet aggregation can significantly contribute to thrombosis at high shear in both operating modes (FIG. 9).

Platelets have a significant role in thrombus formation and one of the advantages of this microfluidic device 100 is that it also can be optionally integrated with automated optical microscopy to quantify platelet aggregation for lab diagnostics and to guide anti-platelet therapy in the clinic. As proof of concept, two platelet activation inhibitors, aspirin (500 μM) and prasugrel (25 μg/ml), were added to recalcified citrated human blood along with fluorescently-labeled autologous platelets; these two drugs are used clinically to treat acute coronary syndromes. The blood was then pumped through the microchannels 110 of the microfluidic device 100 at a constant shear rate of 1250 sec$^{-1}$ (50 dynes/cm$^2$), and scanned a region (24.8×7.5 mm) of one microchannel 110 immediately after occlusion was detected (FIG. 5A,B). In each experiment performed (n=4), the treatment with this drug combination increased the clotting times, $T_{pg}$ and $T_{pf}$, which is consistent with past studies using other clotting assays. On average, the clotting times increased by 13.02% and 6.79%, respectively, in the microfluidic device 100 (FIG. 5C). These studies also revealed that the number of large platelet aggregates was reduced by about 45% (p<0.05, n=5) due to the addition of the drug combination (FIG. 5D).

As is known, the pathophysiology of blood coagulation involves interplay among blood components, the adhesion surface, and fluid dynamics, now popularly known as the Virchow's triad. Clearly, hemostasis is dynamic in nature in that blood-surface interactions leading to thrombosis and fibrinolysis occur in the presence of blood flow. More specifically, independent of soluble clotting agonists, thrombus formation and platelet aggregation is enhanced due to shear gradients arising from acceleration and deceleration of flow at stenotic regions and clotting is most pronounced post-stenosis, where the flow decelerates. However, the agonists, such as collagen or von Willebrand factor (vWf), may also contribute in stabilizing the clot.

Using this microfluidic device 100, distinct shear rates, gradients of shear and relevant hemodynamics can be created that permit measurement of normal and abnormal coagulation responses under more physiological conditions, and this potentially could be carried out in the hematology laboratory or elsewhere, such as at a clinic, doctor's office, or patient's bedside. This device is flexible in operation, for it will afford the physician or clinician to pre-select key parameters such as blood additives (anti-coagulants, drugs, activators, etc.), governing shear rate, microchannel topology (for e.g., a combination of width, height and length to get desirable surface-to-volume ratio at any fixed shear rate) and number of independent microchannels to use. These decisions may be based on the pathology, disease, or condition (if any are known) under investigation (e.g., deficiency in platelet function would advantageously indicate operation at a higher shear since that is where platelets respond most, a suspected venous thrombosis would advantageously operate at a lower shear to minimize impact of platelets on the result). In accord with the present concepts, real-time evolution of blood clots can be recorded and quantified, which is not possible with the current gold standard tests. The blood can be pumped in one of two operating modes (constant pressure or constant flow) that can be selected to mimic the function of the vasculature in vivo—constant flow rate or infusion where exponential growth of pressure is recorded, or alternatively, constant pressure where sigmoidal decay in flow is recorded. In yet other aspects, it may be possible to operate the constant pressure and constant modes in conjunction with one another.

By applying this biomimetic approach to measuring coagulation, the present inventors presented and empirically validated general phenomenological mathematical models that predict dynamics of thrombus formation in both operating modes of blood injection (FIGS. 1, 2). Although coagulation biology is complex and yet to be described completely, it involves non-linear interplay between multiple pro-coagulation and fibrinolytic factors along with platelets. Due to this complexity coupled with the influence of hemodynamic shear forces, an aggregating thrombus can occasionally break and embolize in vivo, and this can be detected in the microfluidic device 100 as measured by occasional fluctuations of growing pressure or decaying flow when blood coagulates (FIG. 2). However, the analytical models presented herein, being global, predict the empirical observation accurately if the data is recorded for the entire clotting process (FIG. 6) and enable the user to extract relevant characteristic parameters that quantitatively define the clotting time of blood under these different physiological conditions (FIG. 3). Unlike current diagnostic tests that provide only one output as the final clotting time, the present concepts provide two characteristic clotting times of the coagulation cascade: time when clotting is actively accelerating and time when the clot has fully occluded the flow (FIG. 3).

The concentration of anticoagulant and the shear rate (and gradient) are the two major determinants of these clotting times when measuring and monitoring of thrombogenicity. The inventors found that the clotting times increase exponentially with the concentration of unfractionated heparin and its sensitivity values are consistent with those determined by other standard tests (FIG. 4A-B, FIG. 8). Thus, the data strongly suggest that the microfluidic device 100 can be utilized in the clinic as an alternative and more quantitative instrument for anti-coagulation monitoring.

When clotting times were analyzed in response to varying shear, the accuracy of the disclosed power-exponential mathematical model (FIG. 7) was confirmed. However, different clotting behaviors were observed when constant flow and constant pressure mode of blood injection were utilized (FIG. 4C-D), which are believed to be attributed to the fact that under constant flow, local shear and Reynolds number can rise to much higher levels at sites where clots form and begin to occlude the channel lumen, as occurs in partially occluded vessels in vivo. These abnormally high shear stresses also can induce thrombi and platelet aggregates to break apart and be released as emboli. The finding that clotting times are higher in the infusion mode compared to the pressure mode in the shear regime that is below physiological can therefore be explained if platelet activation and aggregation do not dominate over embolization at low shear. Also, at low shear in the constant pressure mode, it is possible that fibrinogen diffusion is significant, like in venous blood vessels as the model predicts (FIG. 9). Importantly, this is in contrast to in vitro clotting assays that lack the ability to differentiate between venous and arterial thrombosis. Based on these observations, it is believed that the pressure-driven flow of whole blood, that mimics in vivo thrombosis better at low shear rates, can be particularly suitable for monitoring of deep vein thrombosis (DVT) whereas it is believed the standard infusion-based syringe pump could can be particularly suitable for monitoring arterial thrombosis (AT), which may be validated in further testing (e.g., by analyzing specific biomarkers of these conditions, such as using D-dimer and neutrophil extracellular traps (NETs), which are hallmarks of DVT).

Based on the results disclosed herein, the relationships of clotting times with respect to heparin concentration and shear can be combined to produce the following analytical relationship of clotting time for the infusion mode of pumping blood:

$$(T_{pg}, T_{pf}) = A_{(T_{pg},T_{pf})} e^{B_{(T_{pg},T_{pf})} C_{uh} - C_{(T_{pg},T_{pf})}^{\gamma}} \quad (3)$$

Similarly for the pressure mode, the relationship is as follows:

$$(T_{qg}, T_{qf}) = A_{(T_{qg},T_{qf})} \gamma^{\omega} e^{B_{(T_{qg},T_{qf})} C_{uh} - C_{(T_{qg},T_{qf})}^{\gamma}} \quad (4)$$

The model equations (3) and (4) can fit in equations (1) and (2), respectively, to determine the anticoagulant- and shear-dependent temporal dynamics of coagulation independent of system properties. The constants appearing in these equations (A, B, C and w) are patient specific and may depend upon blood properties that can be empirically determined by curve fitting the analytical equations (1) and/or (2). Thus, the patient-specific constants in equations (3) and (4) are derived from the pressure curve and/or flow curve obtained when the patient's blood sample is allowed to clot and the resulting growth in pressure and/or decay in flow, as applicable, is fit to equations (1) and/or (2) to extract clotting times. These clotting times are functions of, for example, shear and heparin concentration and these parameters, being known in the test performed, can then permit comparison of the clotting time extracted to a standard calibrated clotting time curve (e.g., a baseline curve for the patient, a standard population curve, etc.). In the clinic, these constants might be regularly monitored by the clinician to determine the clotting status of a patient undergoing anti-coagulation therapy or even routine medical examination. For example, responsive to changes in a patient, these patient-specific constants can increase or decrease over time, as these patient-specific constants can be influenced by or depend on other patient-specific markers (e.g., exercise, cholesterol, dietary habits, etc.). Thus, in accord with the present concepts, the clinician may utilize changes in such patient-specific constants as a diagnostic tool to relate such changes to, for example, a clinical manifestation of disease (e.g., arteriosclerosis, etc.), a suggestion of a particular susceptibility, and/or a desirability for additional testing to better characterize the results. As one example, if a 35-yr old female patient's "A" constant value is much lower or higher (e.g., a 50% decrease or increase) as compared to what would be normally observed for that patient (or for a selected population sample inclusive of 35-yr old females), such deviation may correlate to the a certain malady or susceptibility and follow up tests could be suggested and/or a therapy determined responsive to such deviation. In healthy patients, both clotting parameters representing growth and saturation of clot formation follow similar trends when heparin concentration or shear rate is varied. However, it is possible that novel anti-coagulants and anti-platelet drugs produce different behaviors in clotting dynamics, and measurement of the two clotting parameters will enhance sensitivity and specificity of diagnosis and treatment.

By adding an automated imaging protocol, the microfluidic device 100 can be extended to simultaneously measure large platelet aggregates, so it can be used to monitor adjuvant anti-platelet therapy. This method could also be combined with other microscopy techniques, such as confocal imaging or on-chip flow cytometry, to enable more sensitive analysis of platelet activity, and to explore effects of other platelet activators (e.g., collagen, tissue factors), thus enabling the analysis of platelet activation led thrombosis independent of fibrinogen-thrombin led thrombosis. These phenomenological analytical models can be further advanced by incorporating influences of other cellular components of blood, such as leucocytes and erythrocytes, on the clotting times as well. Being a global and quantitative coagulation test, the microfluidic device 100, and the relations disclosed here (Eq. (1)-Eq. (4)), offer a potential way to tackle more complex diseases, such as sepsis and sickle cell anemia, where other cells (e.g., bacteria and sickled erythrocytes) also contribute to the coagulation response. Further, the thrombus monitoring device can be operated, ex vivo, by directly attaching it to catheters or extra-corporeal devices and thus enabling analysis if native blood not drawn in any form of anti-coagulant In view of the above, the microfluidic coagulation device 100 presented here is simple to operate, automated, and multifunctional in that it also can be used to analyze platelet aggregation in combination with the relations disclosed herein (Eq. (1)-Eq. (4)) and can provide an enhanced, real-time quantitative assay for monitoring whole blood thrombogenicity, such as a patient's bedside, in a clinical laboratory, or even a home-care-based assessment tool.

In accord with another aspect of the present concepts, a method (performed in vivo or in vitro) of assessing an effect of a modifier on blood coagulation (e.g., determination of heparin sensitivity by varying heparin levels, such as was shown in FIGS. 4A-4D, etc.) includes the acts of driving a first portion of a blood sample at a constant flow rate through a first plurality of microchannels 110 formed in a microfluidic device 100 substrate and measuring a pressure, or a variable correlated with pressure, in or across at least one of the first plurality of microchannels while the first portion of the blood sample is moved through the first plurality of microchannels at the constant flow rate. The method further includes the acts of determining a first pressure value at an initiation of flow of the first portion of the blood sample and determining a first time at which a second pressure value of the first portion of the blood sample is determined to be about twice the determined first pressure value of the first portion of the blood sample. The method further includes the acts of determining a second time at which a third pressure value of the first portion of the blood sample is determined to be about (1+e) times the determined first pressure value of the first portion of the blood sample and establishing a coagulation model predictive of channel occlusion for the first portion of the blood sample using the first time and the second time, for the first portion of the blood sample, in accord with the relation in Eq. (1), wherein $T_{pf}$ is the second time and $T_{pg}$ is the first time. The method further includes the acts of driving a second portion of the blood sample at a constant flow rate through a second plurality of microchannels formed in the microfluidic device substrate or another microfluidic device substrate and adding a modifier to one of the second portion of the blood sample or the second plurality of microchannels. The method further includes the acts of measuring a pressure, or a variable correlated with pressure, in at least one of the second plurality of microchannels while the second portion of the blood sample is moved through the second plurality of microchannels at the constant flow rate, determining a first pressure value at an initiation of flow of the second portion of the blood sample, and determining a first time at which a second pressure value of the second portion of the blood sample is determined to be about twice the determined first pressure value of the second portion of the blood sample. The method further includes the acts of determining a second time at which a third pressure value of the second portion of the blood sample is determined to be about (1+e) times the determined first pressure value of the second portion of the blood sample and establishing a coagulation model predictive of channel occlusion for the second portion of the blood sample using the first time and the second time, for the second portion of the blood sample, in accord with the relation of Eq. (1), wherein $T_{pf}$ is the second time and $T_{pg}$ is the first time. The method further includes the acts of comparing the coagulation model predictive of channel occlusion for the first portion of the blood sample to the coagulation model predictive of channel occlusion for the second portion of the blood sample to determine an effect of the modifier (e.g., an effect on overall coagulation time, an effect on a particular constituent element to coagulation, etc.).

In still another aspect of the present concepts, a method (performed in vivo or in vitro) of assessing an effect of a modifier on blood coagulation (e.g., determination of heparin sensitivity by varying heparin levels, such as was shown in FIGS. 4A-4D, etc.) includes the acts of driving a first portion of a blood sample at a constant pressure through a first plurality of microchannels 110 formed in a microfluidic device 100 substrate and measuring a flow rate, or a variable correlated with flow rate, in or across at least one of the first plurality of microchannels while the first portion of the blood sample is moved through the first plurality of microchannels at the constant pressure. The method further includes the acts of determining a first flow rate value at an initiation of flow of the first portion of the blood sample, determining a first time at which a second flow rate value of the first portion of the blood sample is determined to be about twice the determined first flow rate value, and determining a second time at which a third flow rate value of the first portion of the blood sample is determined to be about (1+e) times the determined first flow rate value. The method further includes the act of establishing a first coagulation model predictive of channel occlusion for the first portion of the blood sample using the first time and the second time in accord with the relation of Eq. (2), wherein $T_{qf}$ is the second time and $T_{qg}$ is the first time. The method further includes the act of driving a second portion of the blood sample at a constant pressure through a second plurality of microchannels formed in the microfluidic device substrate or another microfluidic device substrate and adding a modifier to one of the second portion of the blood sample or the second plurality of microchannels.

The modifier may comprise, by way of example, an anti-coagulant (e.g., heparin, a low molecular weight heparin, a direct factor inhibitor, a direct thrombin inhibitor, an antithrombin protein, rivorxaban, apixaban, debigatran, a coumarin, hirudin, lepirudin, bivalirudin, argatroban, dabigatran, batroxobin, hementin, etc.), a food supplement derivative, an anti-platelet drug (e.g., an irreversible cyclooxygenase inhibitor, an adenosine diphosphate (ADP) receptor inhibitor, a phosphodiesterase inhibitor, a glycoprotein IIb/IIIa inhibitor, an adenosine reuptake inhibitor, a thromboxane inhibitor, etc.), or a thrombolytic drug (tissue plasminogen activator (tPA), streptokinase, urokinase, etc.). In accord with the present concepts, the modifier can be any substance, or combination of substances, that may affect one or more aspects of the coagulation cascade or that does, in fact, affect one or more aspects of the coagulation cascade. In accord with the present concepts, the modifier can also comprise a modification of removing any substance, or combination of substances, that may affect one or more aspects of the coagulation cascade or that does, in fact, affect one or more aspects of the coagulation cascade. In accord with yet other aspects of the present concepts, the modifier can also comprise both an addition of one or more substances (e.g., a drug under test) that may affect one or more aspects of the coagulation cascade or that does, in fact, affect one or more aspects of the coagulation cascade and a removal of another one or more substances (e.g., a cell, a cellular component, a protein, etc.) that may affect one or more aspects of the coagulation cascade or that does, in fact, affect one or more aspects of the coagulation cascade (e.g., removing platelets to focus on fibrin in a test of a drug potentially affecting fibrin, etc.).

The method further includes the acts of measuring a flow rate, or a variable correlated with flow rate, in or across at least one of the second plurality of microchannels while the second portion of the blood sample is moved through the second plurality of microchannels at the constant pressure and determining a first flow rate value at an initiation of flow of the second portion of the blood sample. The method further includes the acts of determining a first time at which a second flow rate value of the second portion of the blood sample is determined to be about twice the determined first flow rate value of the second portion of the blood sample and determining a second time at which a third flow rate value of the second portion of the blood sample is determined to be about (1+e) times the determined first flow rate value of the second portion of the blood sample. The method further includes the act of establishing a second coagulation model predictive of channel occlusion for the second portion of the blood sample using the first time and the second time, for the second portion of the blood sample, in accord with the relation of Eq. (2), wherein $T_{qf}$ is the second time and $T_{qg}$ is the first time. The method further includes the act of comparing the coagulation model predictive of channel occlusion for the first portion of the blood sample to the coagulation model predictive of channel occlusion for the second portion of the blood sample to determine an effect of the modifier (e.g., an effect on overall coagulation time, an effect on a particular constituent element to coagulation, etc.).

More generally, the microfluidic coagulation device 100 comprises at least one substrate defining a plurality of microchannels 110 (e.g., 2 microchannels, 3 microchannels, etc.). The microchannels 110 are optionally arranged in parallel, and may be formed in two or three dimensions. By varying the width and height of each microchannel 110, it may comprise a cross-sectional surface area in the range of 125 $\mu m^2$-1.75 $mm^2$, which may be uniform amongst the microchannels, or which may vary between one or more of the microchannels or which may vary even along the same microchannel. The sudden expansions to induce shear gradients (flow acceleration and deceleration) can also be altered accordingly. Moreover, a length, shape, surface treatment and/or path of each microchannel 110 need not be uniform and a length, shape, surface treatment and/or path of one or more microchannels may differ from that of one or more other microchannels. By way of example, one of the plurality of microchannels has a cross-sectional geometry that is 75 $\mu m$ in height and 200 $\mu m$ in width, whereas another one of the plurality of microchannels (or possibly a different portion of the same microchannel) has a cross-sectional geometry that is 150 $\mu m$ in height and 400 $\mu m$ in width. Thus, in accord with one aspect of the microfluidic device 100, at least one of the plurality of microchannels has a first cross-sectional area and at least one of the plurality of microchannels has a second cross-sectional area different than the first cross-sectional area. As another example, in another aspect of the microfluidic coagulation device 100, at least one of the plurality of microchannels has a first surface treatment (e.g., a naturally occurring or synthetic reagent, collagen, a thrombus formation-inducing material, a thrombus formation-inhibiting material, cells, endothelial cells, smooth muscle cells, segmented polyurethane, polyvinyl chloride, or polymethyl-methacrylate, etc.) and at least one of the plurality of microchannels has a second surface treatment different than the first surface treatment.

In accord with the disclosed microfluidic device 100, a first port is provided at a first end portion of the substrate (e.g., a proximal or distal end of the substrate), the first port connecting to an inlet end of the plurality of microchannels, or a channel or microchannel leading to the first end of the plurality of microchannels. A second port is provided at a second end portion of the substrate (e.g., the other of the proximal or distal end of the substrate), the second port connecting to outlet ends of the plurality of microchannels, or channel or microchannel leading to the second end of the plurality of microchannels. In accord with the system depicted in FIG. 1, a pump (e.g., a syringe pump) is attached to a port (e.g., a first port 120a) and configured to apply a differential pressure across the first port to drive a blood sample across the plurality of microchannels 110 at a substantially constant flow rate or constant pressure. In the experimental set-up, the tube 125 connecting the pump to the microfluidic device 100 was bonded to the microfluidic device 100. In other configurations, the port and tube 125 may advantageously comprise quick-lock connectors such as, but not limited to, push-to-connect components or a Luer-Lock® connection fitting.

A first sensing device is configured to determine a pressure value in, or relating to, a pressure across the plurality of microchannels. For example, this first sensing device may comprise one or more pressure sensing devices. In another example, the first sensing device comprises a sensor configured to determine a value relating to a pressure across the plurality of microchannels (e.g., amperage of pump). In yet another example, the pressure sensing device senses the negative pressure while the pump delivers vacuum pressure.

Figure 10:
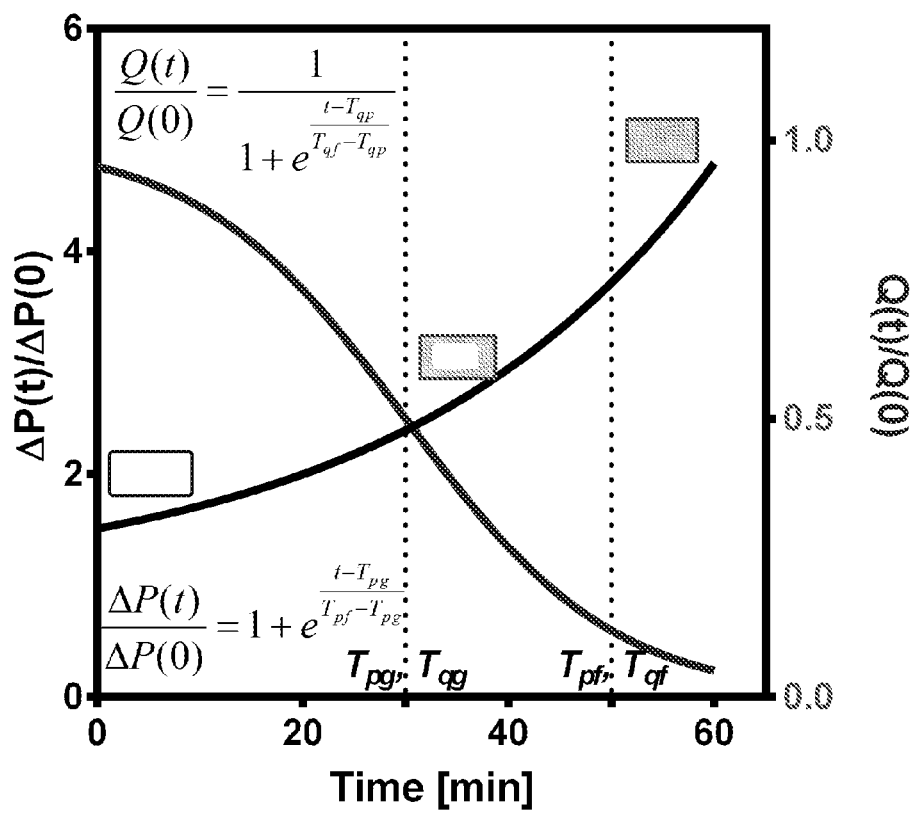
FIG. 10 shows an analytical model for quantitative assessment of whole blood coagulation on a microfluidic device operating in infusion pump mode or pressure pump mode in accord with at least some aspects of the present concepts wherein, in infusion mode, the decay in flow follows a sigmoid trend and wherein, in pressure mode, the pressure grows exponentially, with the clotting times able to be extracted by fitting the equations of the analytical model to these measurements respectively.

As previously noted, FIG. 10 shows an analytical model for quantitative assessment of whole blood coagulation on a microfluidic device 100 operating in infusion pump mode or pressure pump mode in accord with at least some aspects of the present concepts wherein, in infusion mode, the pressure grows exponentially and wherein, in pressure mode, the decay in flow follows a sigmoid trend, with the clotting times able to be extracted by fitting the equations of the analytical model to these measurements respectively. Also shown by a vertical dashed line at approximately 30 minutes are the times $T_{pg}, T_{qg}$, which represent physiologically the growth phase of clotting under constant flow and constant pressure, respectively. Also shown by a vertical dashed line at approximately 50 minutes are the times $T_{pf}, T_{qf}$, which represent physiologically, the saturation phase of clotting under constant flow and constant pressure, respectively. Superimposed on FIG. 10 are representations of cross-sections of the microchannels 110 at T=0 (no clotting), $T=T_{pg}, T_{qg}$ (growth phase, showing partial occlusion of the cross-section), and $T=T_{pf}, T_{qf}$ (saturation phase, at least substantially complete occlusion).

FIG. 11 shows whole blood, drawn in sodium citrate, perfused through the microfluidic device 100 of FIG. 1, and ΔP-Q response curve is plotted to estimate ΔP(0) and Q(0) in infusion mode and pressure mode of operation respectively in accord with at least some aspects of the present concepts.

Figure 12:
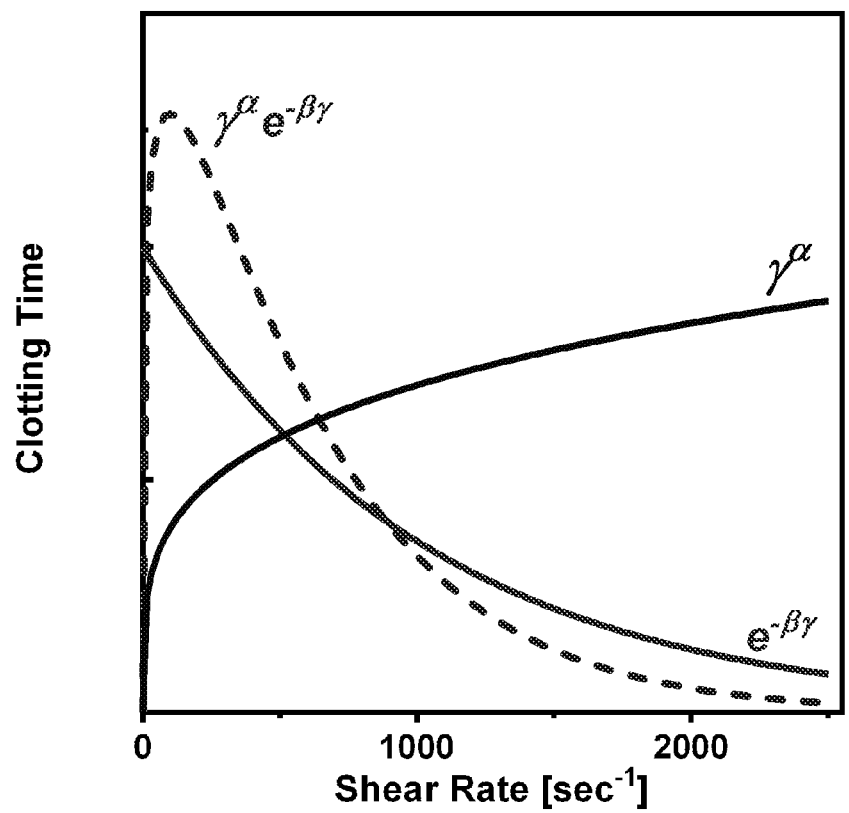
FIG. 12 shows an analytical model to predict the clotting time of whole blood in the coagulation monitoring microfluidic device as a function of shear rate/stress in accord with at least some aspects of the present concepts.

FIG. 12 shows an analytical model to predict the clotting time of whole blood in the coagulation monitoring microfluidic device as a function of shear rate/stress in accord with at least some aspects of the present concepts.

The microfluidic coagulation device 100 shown in FIG. 1 advantageously comprises an attendant computer system, comprising a controller including one or more processors, a bus or other communication mechanism coupled to the one or more processors for communicating information, and a main memory (e.g., RAM) and/or other dynamic storage device, coupled to the bus for storing information and instructions to be executed by processor. This computer system is still further advantageously integrated together with the pump and control systems to enable computer control of the pump operation and sensor data collection. The main memory also may be used for storing temporary variables (e.g., pressure, flow rate, time, etc.) or other intermediate information during execution of instructions to be executed by the controller. Such computer system also includes ROM or other static storage device coupled to the bus for storing static information and instructions for processor. A physical computer-readable storage device, such as a solid-state memory device, is provided and coupled to the bus for storing information. The computer system is also coupled via the bus to one or more display devices (e.g., flat screen display, touch screen, etc.), one or more input devices (keypad, keys, mouse, etc.). In accord with the disclosed methods, in at least some aspects, the methods are implemented utilizing the computer system in response to controller executing one or more sequences of one or more instructions contained in a physical memory device attached to the bus, such as the main memory. Execution of the sequences of instructions causes the controller to perform at least some of the process steps described herein. By way of example, the memory device(s) bear instructions configured to cause the controller to determine, in combination with inputs from the sensing device(s) and a timer, a first pressure value at an initiation of flow, a first time at which a second pressure value is determined to be about twice the determined first pressure value, and a second time at which a third pressure value is about (1+e) times the determined first pressure value. The memory device(s) also bear instructions configured to cause the controller to determine to establish a patient coagulation model predictive of channel occlusion in accord with the relation of Equation (1), above. Similarly, in another aspect, the memory device(s) bear instructions configured to cause the controller to determine, in combination with inputs from the sensing device(s) and a timer, a first flow rate value at a first time corresponding to an initiation of flow, a second time at which a second flow rate value is determined to be about half the determined first flow rate value, a third time at which a third flow rate value is determined to be about (1+e) times lesser than the determined first flow rate value, and a patient coagulation model predictive of channel occlusion governed by the relation of Equation (2), above.

The term "computer-readable medium" as used herein refers to any physical medium that participates in providing instructions to processor(s) for execution (e.g., non-volatile media, volatile media, magnetic media, optical media, solid state media, etc.). The computer system utilized in combination with the microfluidic device 100 also advantageously, but optionally, includes a communication interface coupled to the bus, such communication interface providing a two-way data communication coupling to a network link (e.g., an integrated services digital network (ISDN) card, modem, local area network (LAN) card, wireless link, etc.). The network link provides data communication through one or more networks to other data devices (e.g., the network link may provide a connection through local network to a host computer or to data equipment operated by an Internet Service Provider (ISP)) and the computer system is configured to send and receive data through the network(s), network link(s), and communication interface(s).

It is further noted that the present concepts enable a given patient therapy (e.g., a self-infusions, home care, clinic care, remote health monitoring, etc.) to be modified in real-time. A physician, medical care provider, nurse (or potentially a trained patient) is able to track progress of therapy with the disclosed microfluidic coagulation device 100 and developed equations (1)-(4). For example, while a patient is receiving an infusion (e.g., BeneFIX®, Rixubis, etc.) to provide a therapeutic effect as to a particular malady (e.g., Hemophilia B, etc.), the physician or nurse (or patient) can track the progress of the therapy during the infusion to determine efficacy for that particular patient at that particular time, rather than relying on less precise population estimates. Particularly for expensive treatment protocols (e.g., Factor IX replacement, etc.), the real-time coagulation assessment provided in accord with the present concepts potentially enables treatment to be stopped when an actual, appropriate hemostatic balance has been achieved, rather than relying on gross estimates (or over-estimates) for an infusion dosage required, thus reducing both the cost of treatment (e.g., it could be determined that 500 iU was not needed and that 250 iU was therapeutically sufficient) and the risk of potentially attendant side effects. Continuing with the example of a patient having Factor IX deficiency, real-time changes in the patient's Factor-IX levels (e.g., responsive to diet, ingested supplement, medicine, etc.) may yield a generalized dosing requirement insufficient or, conversely, if a patient's generalized dosing requirement is determined in a clinic at a time at which the patient's Factor-IX levels are suppressed from a typical baseline (e.g., responsive to diet, ingested supplement, medicine, etc.), the prescribing dosing may be more than would be required to achieve the desired therapeutic benefit. Thus, the present concepts permit tailoring of a therapeutic treatment, in real-time, to the specific patient (e.g., human or animal).

These present concepts present many potential applications. In general, coagulation monitors of various types may be used in the diagnosis of thrombogenic disorders (e.g., atherosclerosis, deep venous thrombosis, bleeding disorders, etc.), direct intravascular coagulation (e.g., sepsis, sickle cell disease, trauma, etc.), blood transfusion, hemofiltration, cardiac therapy (e.g., stents, angioplasty, etc.) and monitoring the dosage of anti-coagulation therapy for any of the condition described above. In addition, coagulation monitoring devices are used in drug development research and assays to determine platelet function, etc. The microfluidic device 100 disclosed herein may be used in any of the above applications or settings. Moreover, the disclosed microfluidic device 100 and systems and methods relating thereto, can be performed in such applications or settings at either constant flow or constant pressure driven flow, or potentially both constant flow and constant pressure driven flow.

By way of example, the disclosed microfluidic device 100 and systems and methods relating thereto may be advantageously utilized in the applications of (1) anti-coagulation therapy, (2) anti-platelet therapy, (3) platelet function tests, (4) determination of surface thrombogenicity, and (5) shear stress response. As to anti-coagulation therapy, the present concepts may be applied, for example, to monitor the dosage of and efficacy of both traditional anti-coagulants, such as heparin and warfarin, and new or developmental drugs such as, but not limited to, dabigatran, lepirudin, apixaban, and/or rivaroxaban. As to anti-platelet therapy, the present concepts may be applied, for example, to monitor the dosage of and/or efficacy of anti-platelet drugs such as, but not limited to, aspirin, rofecoxib, valdecoxib, clopidogrel, prasugrel and/or abciximab. As noted above, the microfluidic device 100 and associated system and methods permit dosage to be adjusted, and optimized, in real-time during therapy (e.g., by integrating the device and control system to extra-corporeal treatments, by utilizing the device and control system in a bed-side testing unit, etc.) or substantially contemporaneously therewith (e.g., tests can be undertaken at short time-intervals).

As to the platelet function tests, the disclosed microfluidic device 100 and systems and methods relating thereto are able to unravel platelet activation and aggregation biology and biophysics. The platelet integrins can bind collagen, laminin, and fibrinogen. Platelet activation is also associated with release of ADP and serotonin, synthesis of thromboxane, and exposure of phosphatidylserine, which facilitates thrombin generation. Micropatterned surfaces of hemostatically active proteins such as fibrinogen, collagen (I-VIII), vWF, and lipidated tissue factor can be selectively, serially or parallelly coated on partial or full surface of the device and a multiplexed assay can be carried out. This may also include endothelial cells. Platelet aggregation can also be tested by adding variety of platelet agonists to the blood sample that may include ADP, epinephrine, collagen, arachidonic acid, thrombin, ristocetin etcetera. The surface pattern and/or agonist used could help determine the medication of a patient who is taking some form of anti-coagulation drug depending upon condition.

The disclosed microfluidic device 100 and systems and methods relating thereto are further able to be used for determination of surface thrombogenicity. Platelets may interact with naturally occurring material (endothelial cells, collagen) or synthetic material (e.g., polyethylene glycol (PEG), PEO, POE, poly(1,8-octanediol citrate)(POC), etc.) that could determine hemocompatibility of biomedical devices. The microfluidic device 100 can be coated with a variety of such natural and/or or synthetic materials and hemocompatibility of these materials can be determined with this device.

Further, in view of the above, it is to be understood that one or more of the microfluidic device 100 microchannels 110, or portion(s) thereof, can be coated with a variety of such natural and/or or synthetic materials and hemocompatibility of these materials can be determined with this device. For example, one or more microchannels 110 of the microfluidic device 100, or portion(s) thereof, can be coated with a first naturally occurring material (e.g., Type 1 collagen), one or more microchannels of the microfluidic device, or portion(s) thereof, can be coated with a second naturally occurring material (e.g., Type 2 collagen), and one or more microchannels of the microfluidic device, or portion(s) thereof, can be coated with a third naturally occurring material (e.g., Collagen alpha-1(III) chain), and one or more microchannels of the microfluidic device, or portion(s) thereof, can be coated with a synthetic material (e.g., PEG). As another example, one microchannel 110, or portion(s) thereof, is coated with collagen, another microchannel, or portion(s) thereof, is coated with epinephrine and yet another microchannel, or portion(s) thereof, is coated with Thromboxane A2 (TXA2) to enhance assay specificity and sensitivity. In accord with at least some aspects of the present concepts, one or more microchannels 110 can be used as controls, providing known or standardized results to which behavior of one or more other microchannels 110 can be readily compared. In yet other aspects, at least some of the microchannels of the microfluidic device 100 are adapted to provide diagnostic tools, such as to detect the D-dimer antigen as a marker to rule out the presence of venous thromboembolism (e.g., deep vein thrombosis (DVT) and/or pulmonary embolism (PE)), or research tools, such as to study extracellular matrix (ECM) induced clot formation.

The microfluidic device 100 may accordingly comprise, for example, a plurality of microchannels 110 having one or more different coatings and/or surface treatments that may comprise one or more natural materials, one or more synthetic materials, or a combination of one or more natural materials (e.g., cells, proteins, molecules, enzymes, receptors, etc.) and one or more synthetic materials.

Additionally, the disclosed microfluidic device 100 and systems and methods relating thereto are able to be used for determination of shear stress response. Coagulation is a function of shear stress and the disclosed microfluidic device 100 can allow a relevant shear stress to be applied to quantitatively assess thrombogenicity in the range 75-2500 $sec^{-1}$.

Recent mechanistic studies have shown that thrombus formation and platelet aggregation at the site of vascular injury or atherosclerotic lesions, in vivo, are caused by changes in the fluid dynamics of blood flow. More specifically, independent of soluble clotting agonists, thrombus formation and platelet aggregation is enhanced due to shear gradients (rate of change of shear stress) arising from acceleration and deceleration of flow at stenotic regions and clotting is most pronounced post-stenosis, where the flow decelerates. However, the agonists, such as collagen or von Willebrand factor (vWf), may also contribute in stabilizing the clot. FIG. 13A shows another example of a microfluidic device 100, in accord with at least some aspects of the present concepts, comprising a microchannel 110 geometry that allows the fluid to pass through a converging zone 500 (flow acceleration; prestenosis) near the inlet into multiple lanes made of channels of constant width 520 that have curves and straight sections. The fluid then exits through a diverging section 540 (flow deceleration; post-stenosis) into a common outlet.

Figure 13B:
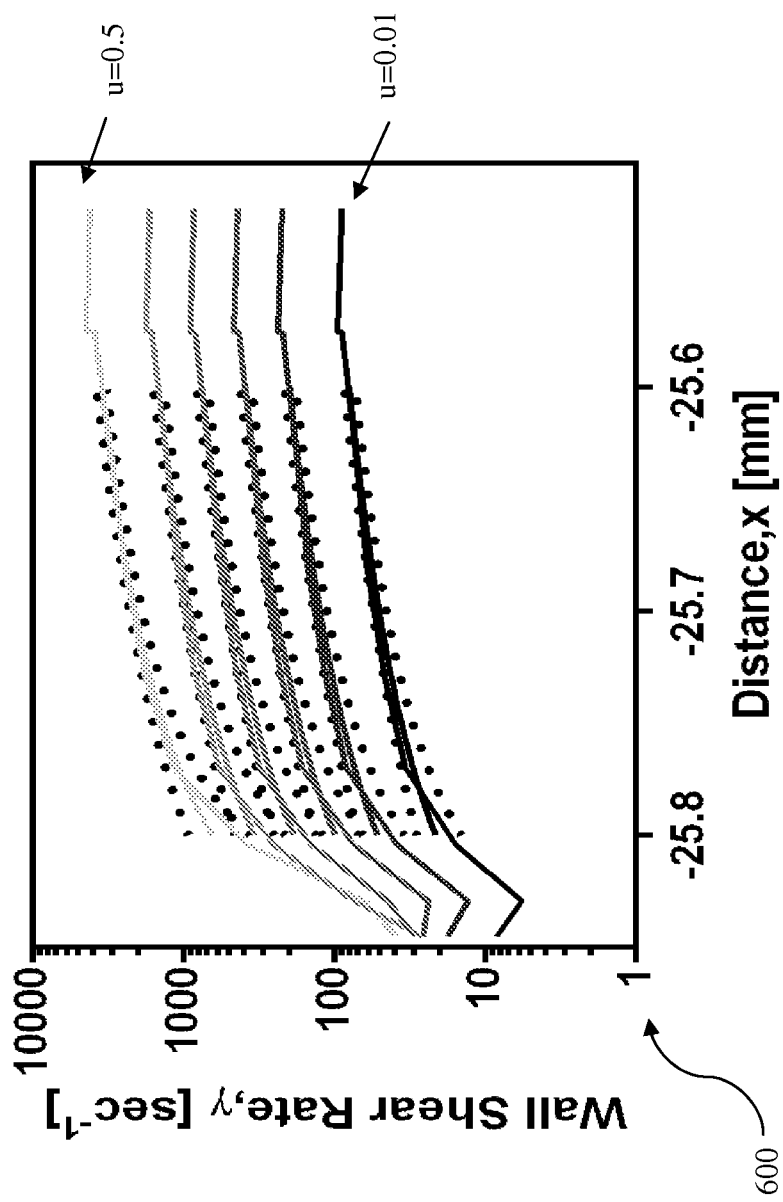
Figure 13C:
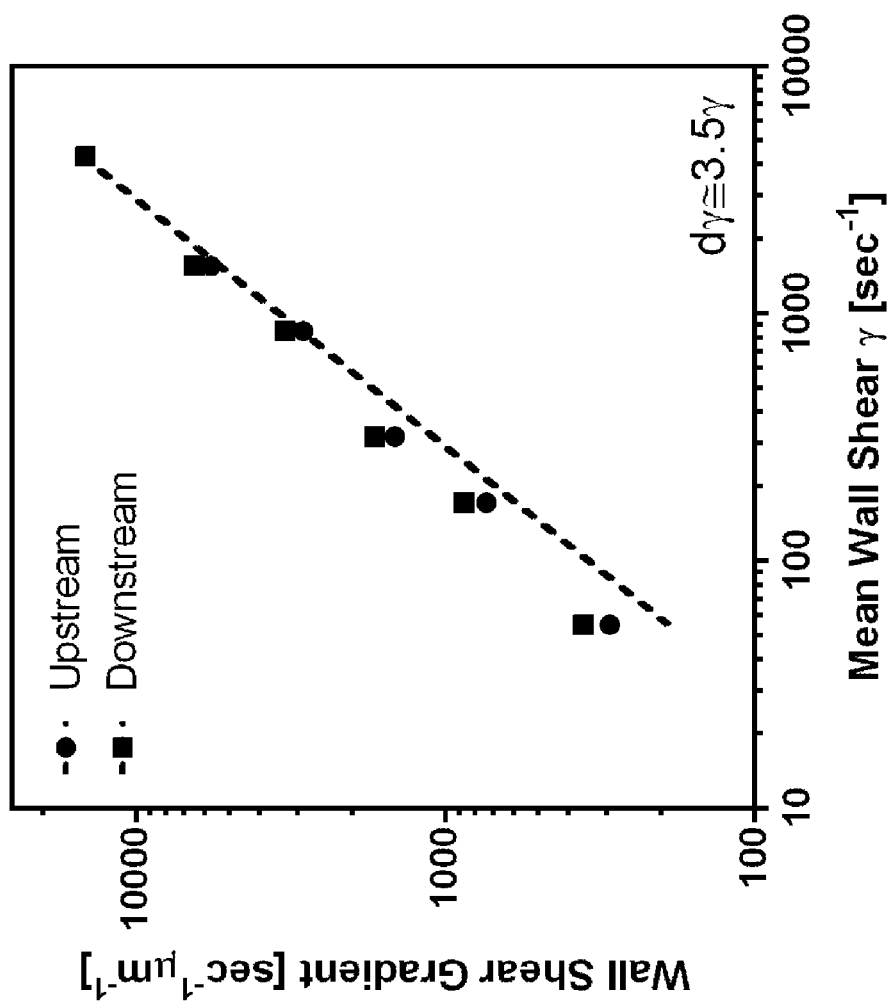

As shown in FIGS. 13A-13C, finite element computational modeling of non-Newtonian blood flow, using COMSOL Multiphysics® software, predicts that the wall shear rate increases dramatically at the converging section 500 (see reference numeral 600 FIG. 13A, Wall Shear Rate, $\gamma$ [sec$^{-1}$] vs. Distance, x [mm], and the corresponding exploded view of reference numeral 600 in FIG. 13B). The computational modeling also predicts that the wall shear rate will remain steady in the constant-width section 520 and decrease dramatically at the diverging section 540. In the computational model, the inlet boundary condition imposed is P=0 (no pressure) and the outlet boundary condition is of a specified normal velocity (no flow across the channel and only along the longitudinal/vertical direction).

In the Wall Shear Rate, $\gamma$ [sec$^{-1}$] vs. Distance, x [mm] plot at the bottom of FIG. 13A and in FIG. 13B, plots are shown (from top to bottom) for values of normal velocity, u=0.5, 0.2, 0.1, 0.05, 0.025 and 0.01, [mm/sec] respectively Therefore, in the embodiment of microfluidic device 100 shown in FIG. 13A, the shear rate gradients that are created depend on the mean wall shear that is applied and controlled from an external blood pump. However, the geometry can be altered to have any desirable hemodynamic environment that mimics or exacerbates the functional pathophysiology of atherosclerosis for the purpose of improving blood based analytical devices.

For the microfluidic device 100 of FIG. 13A, it is shown in FIG. 14 that fibrin formation 610 and platelet adhesion 620 are elevated at the converging (upstream) and diverging (downstream) sections 500, 540 of the microfluidic device, where the shear gradient is very high (as shown in FIG. 13C), as compared to the remaining constant-width section 520 of the device. Interestingly, as shown in FIG. 13C and FIG. 14, blood clotting is maximized at the diverging (downstream) section 540, which mimics the post-stenotic geometry of atherosclerosis. Therefore, the disclosed microfluidic device 100 allows blood clotting to occur and to be easily visualized in the presence of physiological or pathological shear and shear gradients, inside microchannels 110 that mimic the size of human blood vessels.

Figure 15:
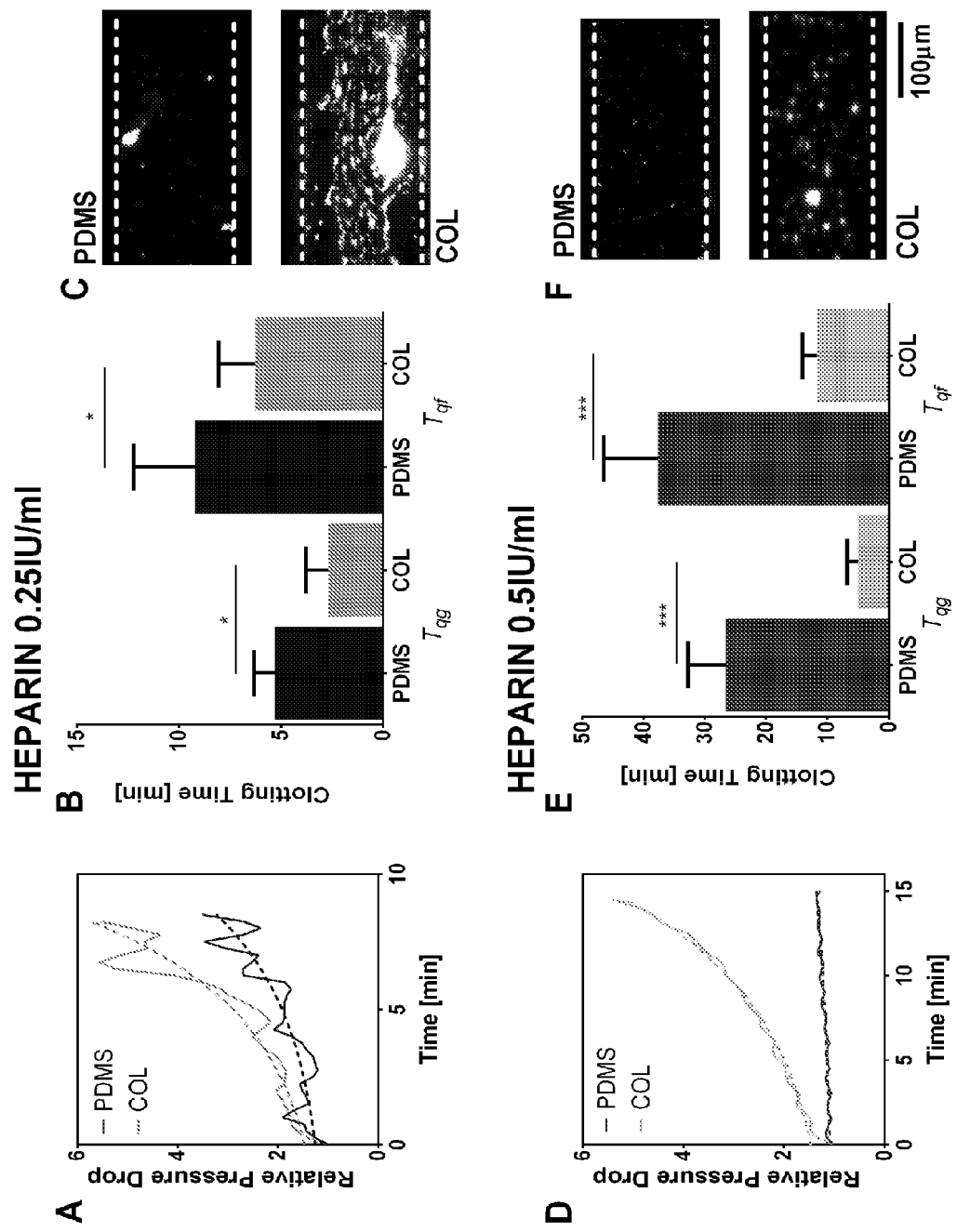
FIG. 15 shows that a collagen coating utilized with the microfluidic device represented in FIGS. 13A-13C reduces clot monitoring assay time to within 2-20 minutes.

As noted above, the microfluidic device 100 can be made of a variety of materials that can be prothrombogenic or anti-thrombogenic. For example, the thrombus formation inside a microfluidic device 100 made of PDMS with no surface alteration of the microchannels 110, when activated by shear gradient alone, such that the maximum gradient achieved is 3.5 times the mean wall shear, results in clotting time in the range of 15-60 minutes depending upon parameters such as, concentration of anticoagulant, applied shear, etc. However, when the microfluidic device 100 microchannels 110 are coated with human collagen I at a concentration of 100 μg/ml, it was found that the clotting time can be reduced to 2-20 minutes and therefore, allowing this tool for a more rapid analysis, when desired, as is shown in FIG. 15.

The thrombus monitoring device can be operated, ex vivo, by directly attaching it to catheters or extra-corporeal devices and thus enabling analysis if native blood not drawn in any form of anti-coagulant.

It is known that equipment used to draw blood, primarily including some type of anticoagulation tube (EDTA, heparin, PPACK etc), changes the blood chemistry that may impact many in vitro hemoanalytical assays, including clotting time tests. Aspects of the disclosed microfluidic device 100, such as that depicted in FIGS. 13A and 14, which require a very small amount of blood and relatively simple instrumentation downstream of the device, can potentially be attached directly to a patient's blood vessel (e.g., via a standard catheter) or integrated to an extra-corporeal device (e.g., a cardiac pump, ECMO device, dialysis equipment, etc.), thus minimizing the impact of anticoagulation tube and other pre-analytical variables that alter blood function. Thus, native whole blood from a patient can be passed directly to the microfluidic device 100 without need for any external pump, intermediary storage, or treatment (e.g., anti-thrombogenic coatings are not needed and are advantageously omitted).

In accord with the above concepts, the clotting characteristics of a blood sample in the microfluidic device 100 can be tailored by selection of the microchannel 110 geometry (e.g., to alter a shear stress gradient, etc.) and/or selection of optional agonists. As one example, the microfluidic device 100 of FIG. 13A comprises a plurality of microchannels (e.g., more than one microchannel), each of the plurality of microchannels defining a proximal first end (comprising an inlet portion), a medial portion, and a distal second end (comprising an outlet portion). Each of the microchannels 110 is the example of FIG. 13A comprises a converging portion (e.g., preferably comprising a gently converging cross-sectional area over a first length, but potentially comprising a step-decrease) where a cross-sectional area of the microchannel decreases from a first cross-sectional area to a smaller second cross-sectional area. Over the medial portion, which may occupy a significant portion of a length of the microchannel 110, a substantially constant cross-sectional area is maintained. A diverging portion (e.g., preferably comprising a gently diverging cross-sectional area over a third length, but potentially comprising a step-increase) is also provided where the cross-sectional area of the microchannel increases from the second cross-sectional area to a larger third cross-sectional area. The third cross-sectional area may be the same as or different from the first cross-sectional area. As with other embodiments of the microfluidic device described herein, the plurality of microchannels 110 may advantageously comprise a first set of one or more microchannels having a first geometry over at least a portion of its length and a second set of one or more microchannels having a second geometry over at least a portion of its length. These first and second sets of one or more microchannels may further optionally comprise the same agonist and/or surface treatments or different agonists and/or surface treatments, as described elsewhere herein.

In other aspects of the present concepts, at least some of the plurality of microchannels 110 may omit either the converging portion or the diverging portion, with the wall shear gradient being selected in the respective one of the converging portion or the diverging portion, or collectively the whole of the microchannel, to achieve a desired hemodynamic environment. Further, although examples are provided herein with converging portions in inlet regions of a microchannel and diverging portions in outlet regions of the microchannels, such converging portions and diverging portions are not limited to the periphery of the microchannels and may be disposed anywhere within the microchannels (e.g., in a middle portion of the microchannels) and may comprise any number of such converging portions and diverging portions (e.g., two sets or three sets of converging portions and diverging portions).

As disclosed herein, substantially constant flow and substantially constant mean that the flow or pressure, respectively, may vary within a range about an average or mean flow or pressure value, such as by +/−10%, +/−5%, +/−2%, or +/−1% depending upon the specifications of instrumentation/equipment used to set the substantially constant flow or pressure.

Each of the disclosed embodiments and obvious variations thereof are contemplated as falling within the spirit and scope of the claimed invention, aspects of which embodiments are set forth in the following claims.

What is claimed is:

1. A microfluidic coagulation device, comprising:
    at least one substrate defining a plurality of microchannels;
    a first port at a first end portion of the substrate, the first port connecting to first ends of the plurality of microchannels;
    a second port at a second end portion of the substrate, the second port connecting to second ends of the plurality of microchannels;
    a first sensing device configured to determine a pressure value in, or relating to, a pressure across the plurality of microchannels;
    a timer; and
    a controller configured to determine, in combination with the first sensing device and the timer, a first pressure value at an initiation of flow, a first time at which a second pressure value is determined to be about twice the determined first pressure value, and a second time at which a third pressure value is about (1+e) times the determined first pressure value, and further configured to establish a subject coagulation model predictive of channel occlusion in accord with the relation $$\frac{\Delta P(t)}{\Delta P(0)} = 1 + e^{\frac{t - T_{pg}}{T_{pf} - T_{pg}}}$$

wherein $T_{pf}$ is the second time and $T_{pg}$ is the first time, and wherein a differential pressure or flow rate/shear applied across the first port drives a blood sample across the plurality of microchannels at a substantially constant flow rate.

2. The microfluidic coagulation device according to claim 1, further comprising:
    an instrument that causes differential pressure or flow rate/shear applied across the first port to drive a blood sample across the plurality of microchannels at a substantially constant flow rate,
    wherein the instrument that generates the differential pressure or flow is a pump.

3. The microfluidic coagulation device according to claim 2, wherein the instrument is a syringe pump.

4. The microfluidic coagulation device according to claim 1, wherein the at least some of the plurality of microchannels comprise a cross-sectional surface area between about 125 $\mu m^2$-1.75 $mm^2$.

5. The microfluidic coagulation device according to claim 1, wherein the at least some of the plurality of microchannels comprise a maximal hydraulic diameter between about 25 $\mu m$-5 mm.

6. The microfluidic coagulation device according to claim 5, wherein at least some of the plurality of microchannels have a maximal dimension between about 75 $\mu m$-200 $\mu m$.

7. The microfluidic coagulation device according to claim 1, wherein at least one of the plurality of microchannels has a first cross-sectional area and at least one of the plurality of microchannels has a second cross-sectional area different than the first cross-sectional area.

8. The microfluidic coagulation device according to claim 1, wherein at least a portion of a first microchannel has a first surface treatment.

9. The microfluidic coagulation device according to claim 8, wherein at least a portion of a second microchannel has a second surface treatment different than the first surface treatment.

10. The microfluidic coagulation device according to claim 9, wherein at least one of the first surface treatment or second surface treatment comprises one of a naturally occurring or synthetic reagent, collagen, a thrombus formation-inducing material, a thrombus formation-inhibiting material, a platelet activating material, and platelet inhibiting material, a fibrin network forming material, a fibrin network disrupting material, cells, endothelial cells, smooth muscle cells, segmented polyurethane, polyvinyl chloride, or polymethyl-methacrylate.

11. The microfluidic coagulation device according to claim 1, wherein the shear rate is between 75 $sec^{-1}$ and 5000 $sec^{-1}$.

12. The microfluidic coagulation device according to claim 1, further comprising:
    an imaging system configured to image at least one portion of at least one of the plurality of microchannels.

13. The microfluidic coagulation device according to claim 12, wherein the imaging system comprises an automated imaging protocol.

14. The microfluidic coagulation device according to claim 13, wherein the imaging system comprises confocal imaging or on-chip flow cytometry.

15. The microfluidic coagulation device according to claim 13, wherein the imaging system is configured to measure platelet aggregates or to image effects of platelet activators, cellular components of blood, or cells on coagulation.

16. The microfluidic coagulation device according to claim 1, wherein the differential pressure applied across the first port to drive a blood sample across the plurality of microchannels at a substantially constant flow rate comprises a patient's blood pressure.

17. A microfluidic coagulation device, comprising:
    at least one substrate defining a plurality of microchannels;
    a first port at a first end portion of the substrate, the first port connecting to first ends of the plurality of microchannels;
    a second port at a second end portion of the substrate, the second port connecting to second ends of the plurality of microchannels;

a first sensing device configured to determine a flow rate in, or relating to, the plurality of microchannels,
a timer; and
a controller configured to determine, in combination with the first sensing device and the timer, (i) a first flow rate value at a first time corresponding to an initiation of flow, (ii) a second time at which a second flow rate value is determined to be about half the determined first flow rate value, (iii) a third time at which a third flow rate value is determined to be about (1+e) times lesser than the determined first flow rate value, and (iv) a blood coagulation model predictive of channel occlusion governed by the relation $$\frac{Q(t)}{Q(0)} = \frac{1}{1 + e^{\frac{t - T_{qg}}{T_{qf} - T_{qg}}}}$$

wherein $T_{qf}$ is the third time and $T_{qg}$ is the second time,
wherein a differential pressure is applied to the first port to drive a blood sample across the plurality of microchannels.

18. The microfluidic coagulation device according to claim 17, further comprising:
an instrument configured to apply a differential pressure to the first port and configured to drive a blood sample across the plurality of microchannels,
wherein the differential pressure is generated by a pump.

19. The microfluidic coagulation device according to claim 18, wherein the pump is a syringe pump or a peristaltic pump or any other constant flow delivering pump.

20. The microfluidic coagulation device according to claim 18, wherein the shear rate is between 75 sec$^{-1}$ and 5000 sec$^{-1}$.

21. The microfluidic coagulation device according to claim 17, wherein the at least some of the plurality of microchannels comprise a cross-sectional surface area between about 125 µm$^2$-1.75 mm$^2$.

22. The microfluidic coagulation device according to claim 17, wherein the at least some of the plurality of microchannels comprise a maximal dimension between about 25 µm-5 mm.

23. The microfluidic coagulation device according to claim 17, wherein at least some of the plurality of microchannels have a maximal dimension between about 75 µm-200 µm.

24. The microfluidic coagulation device according to claim 17, wherein at least one of the plurality of microchannels has a first cross-sectional area and at least one of the plurality of microchannels has a second cross-sectional area different than the first cross-sectional area.

25. The microfluidic coagulation device according to claim 17, wherein at least a portion of one of the plurality of microchannels has a first surface treatment.

26. The microfluidic coagulation device according to claim 25, wherein at least a portion of another one of the plurality of microchannels has a second surface treatment different than the first surface treatment.

27. The microfluidic coagulation device according to claim 26, wherein at least one of the first surface treatment or second surface treatment comprises one of a naturally occurring or synthetic reagent, collagen, a thrombus formation-inducing material, a thrombus formation-inhibiting material, a platelet activating material, and platelet inhibiting material, a fibrin network forming material, a fibrin network disrupting material, cells, endothelial cells, smooth muscle cells, segmented polyurethane, polyvinyl chloride, or polymethyl-methacrylate.

28. The microfluidic coagulation device according to claim 17, further comprising:
an imaging system configured to image at least one portion of at least one of the plurality of microchannels.

29. The microfluidic coagulation device according to claim 28, wherein the imaging system comprises an automated imaging protocol.

30. The microfluidic coagulation device according to claim 29, wherein the imaging system comprises confocal imaging or on-chip flow cytometry.

31. The microfluidic coagulation device according to claim 29, wherein the imaging system is configured to measure platelet aggregates or is configured to image effects of platelet activators, cellular components of blood, or cells on coagulation.

32. The microfluidic coagulation device according to claim 17, wherein the wherein a differential pressure is applied to the first port to drive a blood sample across the plurality of microchannels comprises a patient's blood pressure.

33. A method of assessing at least some aspects of a subject's coagulation from a blood sample taken from the subject, the method comprising the acts of:
driving the blood sample from the subject at a substantially constant flow rate through a plurality of microchannels formed in a microfluidic device substrate;
measuring a pressure, or a variable correlated with pressure, in at least one of the plurality of microchannels while the blood sample is moved through the plurality of microchannels at the substantially constant flow rate;
determining a first pressure value at an initiation of flow;
determining a first time at which a second pressure value is determined to be about twice the determined first pressure value;
determining a second time at which a third pressure value is determined to be about (1+e) times the determined first pressure value;
establishing a coagulation model predictive of channel occlusion for the subject using the first time and the second time in the relation $$\frac{\Delta P(t)}{\Delta P(0)} = 1 + e^{\frac{t - T_{pg}}{T_{pf} - T_{pg}}}$$

wherein $T_{pf}$ is the second time and $T_{pg}$ is the first time; and
recording, on a physical storage medium, the established subject-specific coagulation model.

34. The method of assessing coagulation of a subject's blood according to claim 33, the method further comprising the act of:
driving the blood sample from the subject through a direct connection, through a catheter or an extra-corporeal device, from the patient to the microfluidic device.

35. The method of assessing coagulation of a subject's blood according to claim 33, the method further comprising the act of:
determining at least one of a dosage of a therapeutic drug for the subject, a concentration of a therapeutic drug for the subject, or a frequency of an application of a therapeutic drug for the subject responsive to the established subject-specific coagulation model.

36. The method of assessing at least some aspects of a subject's coagulation according to claim 33, the method further comprising the act of:
imaging at least one portion of at least one of the plurality of microchannels during the coagulation process to provide information relating to the coagulation process.

37. The method of assessing at least some aspects of a subject's coagulation according to claim 36, the method further comprising the act of:
imaging at least one portion of at least one of the plurality of microchannels during the coagulation process to provide information relating to the coagulation process.

38. A method of assessing at least some aspects of a subject's coagulation from a blood sample taken from the subject, the method comprising the acts of:
driving the blood sample at a substantially constant pressure through a plurality of microchannels formed in a microfluidic device substrate;
measuring a flow rate, or a variable correlated with flow rate, in at least one of the plurality of microchannels while the blood sample is moved through the plurality of microchannels at the substantially constant pressure;
determining a first flow rate value at an initiation of flow;
determining a first time at which a second flow rate value is determined to be about twice the determined first flow rate value;
determining a second time at which a third flow rate value is determined to be about (1+e) times the determined first flow rate value;
establishing a subject-specific coagulation model predictive of channel occlusion for the subject using the first time and the second time in the relation $$\frac{Q(t)}{Q(0)} = \frac{1}{1 + e^{\frac{t-T_{qg}}{T_{qf}-T_{qg}}}}$$

wherein $T_{qf}$ is the second time and $T_{qg}$ is the first time; and
recording, on a physical storage medium, the established subject-specific coagulation model.

39. The method of assessing at least some aspects of a subject's coagulation according to claim 38, the method further comprising the act of:
adjusting at least one of a dosage, a concentration, of a frequency of an application of a therapeutic drug for the subject responsive to the established subject-specific coagulation model.

40. The method of assessing at least some aspects of a subject's coagulation according to claim 38, the method further comprising the act of:
determining at least one of a dosage of a therapeutic drug for the subject, a concentration of a therapeutic drug for the subject, or a frequency of an application of a therapeutic drug for the subject responsive to the established subject-specific coagulation model.

41. A method of assessing at least some aspects of a subject's coagulation from a blood sample from the subject, the method comprising the acts of:
driving a first portion of the blood sample for a subject at a substantially constant flow rate through a first plurality of microchannels formed in a first microfluidic device substrate;
measuring a pressure, or a variable correlated with pressure, in at least one of the first plurality of microchannels while the first portion of the blood sample is moved through the first plurality of microchannels at the substantially constant flow rate;
determining a first pressure value at an initiation of flow;
determining a first time at which a second pressure value is determined to be about twice the determined first pressure value;
determining a second time at which a third pressure value is determined to be about (1+e) times the determined first pressure value;
establishing a first subject-specific coagulation model predictive of channel occlusion using the first time and the second time in the relation $$\frac{\Delta P(t)}{\Delta P(0)} = 1 + e^{\frac{t-T_{pg}}{T_{pf}-T_{pg}}}$$

wherein $T_{pf}$ is the second time and $T_{pg}$ is the first time;
recording, on a physical storage medium, the established first subject-specific coagulation model;
driving a second portion of the blood sample for the subject at a substantially constant pressure through a plurality of second microchannel formed in the first microfluidic device substrate or in a second microfluidic device substrate;
measuring a flow rate, or a variable correlated with flow rate, in at least one of the plurality of second microchannels while the second portion of the blood sample is moved through the plurality of second microchannels at the substantially constant pressure;
determining a first flow rate value at an initiation of flow;
determining a first time at which a second flow rate value is determined to be about twice the determined first flow rate value;
determining a second time at which a third flow rate value is determined to be about (1+e) times the determined first flow rate value;
establishing a second subject-specific coagulation model predictive of channel occlusion using the first time and the second time in the relation $$\frac{Q(t)}{Q(0)} = \frac{1}{1 + e^{\frac{t-T_{qg}}{T_{qf}-T_{qg}}}}$$

wherein $T_{qf}$ is the second time and $T_{qg}$ is the first time; and
recording, on the physical storage medium, the established second subject-specific coagulation model.

42. A method of assessing at least some aspects of a subject's coagulation from a blood sample from the subject, the method comprising the acts of:
driving the blood sample at a substantially constant flow rate through a plurality of microchannels formed in a microfluidic device substrate;
measuring a pressure, or a variable correlated with pressure, in at least one of the plurality of microchannels while the blood sample is moved through the plurality of microchannels at the substantially constant flow rate;
determining a first pressure value at an initiation of flow;
determining a first time at which a second pressure value is determined to be about twice the determined first pressure value;
determining a second time at which a third pressure value is determined to be about (1+e) times the determined first pressure value;

establishing a subject-specific coagulation model predictive of channel occlusion; and recording, on a physical storage medium, the subject-specific coagulation model, the subject-specific coagulation model utilizing the relation $$(T_{pg}, T_{pf}) = A_{(T_{pg},T_{pf})} e^{B_{(T_{pg},T_{pf})} C_{uh} - C_{(T_{pg},T_{pf})}^{\gamma}}$$

wherein A, B and C are subject-specific variables relating to blood properties empirically determined by curve fitting the following relation $$\frac{\Delta P(t)}{\Delta P(0)} = 1 + e^{\frac{t-T_{pg}}{T_{pf}-T_{pg}}}$$

and wherein $T_{pf}$ is the second time and $T_{pg}$ is the first time.

43. A method of assessing coagulation of a subject's blood sample, the method comprising the acts of:

driving the blood sample at a substantially constant pressure through a plurality of microchannels formed in a microfluidic device substrate;

measuring a flow rate, or a variable correlated with flow rate, in at least one of the plurality of microchannels while the blood sample is moved through the plurality of microchannels at the substantially constant pressure;

determining a first flow rate value at an initiation of flow;

determining a first time at which a second flow rate value is determined to be about twice the determined first flow rate value;

determining a second time at which a third flow rate value is determined to be about (1+e) times the determined first flow rate value;

recording, on a physical storage medium, a subject-specific coagulation model, the subject-specific coagulation model utilizing the relation $$(T_{qg}, T_{qf}) = A_{(T_{qg},T_{qf})} \gamma^\omega e^{B_{(T_{qg},T_{qf})} C_{uh} - C_{(T_{qg},T_{qf})}^{\gamma}}$$

wherein A, B and C are subject-specific variables relating to blood properties empirically determined by curve fitting the following relation $$\frac{Q(t)}{Q(0)} = \frac{1}{1 + e^{\frac{t-T_{qg}}{T_{qf}-T_{qg}}}}$$

and wherein $T_{pf}$ is the second time and $T_{pg}$ is the first time.

44. A method of assessing an effect of a modifier on blood coagulation, the method comprising the acts of:

driving a first portion of a blood sample at a substantially constant flow rate through a first plurality of microchannels formed in a microfluidic device substrate;

measuring a pressure, or a variable correlated with pressure, in at least one of the first plurality of microchannels while the first portion of the blood sample is moved through the first plurality of microchannels at the substantially constant flow rate;

determining a first pressure value at an initiation of flow of the first portion of the blood sample;

determining a first time at which a second pressure value of the first portion of the blood sample is determined to be about twice the determined first pressure value of the first portion of the blood sample;

determining a second time at which a third pressure value of the first portion of the blood sample is determined to be about (1+e) times the determined first pressure value of the first portion of the blood sample;

establishing a coagulation model predictive of channel occlusion for the first portion of the blood sample using the first time and the second time, for the first portion of the blood sample, in the relation $$\frac{\Delta P(t)}{\Delta P(0)} = 1 + e^{\frac{t-T_{pg}}{T_{pf}-T_{pg}}}$$

wherein $T_{pf}$ is the second time and $T_{pg}$ is the first time;

driving a second portion of the blood sample at a substantially constant flow rate through a second plurality of microchannels formed in the microfluidic device substrate or another microfluidic device substrate;

adding a modifier to one of the second portion of the blood sample or the second plurality of microchannels;

measuring a pressure, or a variable correlated with pressure, in at least one of the second plurality of microchannels while the second portion of the blood sample is moved through the second plurality of microchannels at the substantially constant flow rate;

determining a first pressure value at an initiation of flow of the second portion of the blood sample;

determining a first time at which a second pressure value of the second portion of the blood sample is determined to be about twice the determined first pressure value of the second portion of the blood sample;

determining a second time at which a third pressure value of the second portion of the blood sample is determined to be about (1+e) times the determined first pressure value of the second portion of the blood sample;

establishing a coagulation model predictive of channel occlusion for the second portion of the blood sample using the first time and the second time, for the second portion of the blood sample, in the relation $$\frac{\Delta P(t)}{\Delta P(0)} = 1 + e^{\frac{t-T_{pg}}{T_{pf}-T_{pg}}}$$

wherein $T_{pf}$ is the second time and $T_{pg}$ is the first time; and comparing the coagulation model predictive of channel occlusion for the first portion of the blood sample to the coagulation model predictive of channel occlusion for the second portion of the blood sample to determine an effect of the modifier.

45. The method of assessing an effect of a modifier on blood coagulation according to claim 44, wherein the modifier comprises an anti-coagulant.

46. The method of assessing an effect of a modifier on blood coagulation according to claim 45, wherein the modifier comprises one of heparin, a low molecular weight heparin, a direct factor inhibitor, a direct thrombin inhibitor, an antithrombin protein, rivorxaban, apixaban, debigatran, a coumarin, hirudin, lepirudin, bivalirudin, argatroban, dabigatran, batroxobin, hementin.

47. The method of assessing an effect of a modifier on blood coagulation according to claim 46, further comprising:
 driving a third portion of the blood sample at the substantially constant flow rate through a third plurality of microchannels formed in the microfluidic device substrate or another microfluidic device substrate;
 adding a second modifier to one of the third portion of the blood sample or the third plurality of microchannels;
 measuring a pressure, or a variable correlated with pressure, in at least one of the second plurality of microchannels while the third portion of the blood sample is moved through the third plurality of microchannels at the substantially constant flow rate;
 determining a first pressure value at an initiation of flow of the third portion of the blood sample;
 determining a first time at which a second pressure value of the second portion of the blood sample is determined to be about twice the determined first pressure value of the third portion of the blood sample;
 determining a second time at which a third pressure value of the second portion of the blood sample is determined to be about (1+e) times the determined first pressure value of the third portion of the blood sample;
 establishing a coagulation model predictive of channel occlusion for the second portion of the blood sample using the first time and the second time, for the third portion of the blood sample, in the relation $$\frac{\Delta P(t)}{\Delta P(0)} = 1 + e^{\frac{t - T_{pg}}{T_{pf} - T_{pg}}}$$

wherein $T_{pf}$ is the second time and $T_{pg}$ is the first time; and
 comparing the coagulation model predictive of channel occlusion for the first portion of the blood sample to the coagulation model predictive of channel occlusion for the third portion of the blood sample to determine an effect of the second modifier,
 wherein the second modifier is different than the modifier.

48. The method of assessing an effect of a modifier on blood coagulation according to claim 47, wherein the second modifier is the same substance as the modifier, but comprises a different amount or concentration.

49. The method of assessing an effect of a modifier on blood coagulation according to claim 44, wherein the modifier comprises a food supplement derivative.

50. The method of assessing an effect of a modifier on blood coagulation according to claim 44, wherein the modifier comprises an anti-platelet drug.

51. The method of assessing an effect of a modifier on blood coagulation according to claim 50, wherein the modifier comprises an irreversible cyclooxygenase inhibitor, an adenosine diphosphate (ADP) receptor inhibitor, a phosphodiesterase inhibitor, a glycoprotein IIb/IIIa inhibitor, an adenosine reuptake inhibitor, or a thromboxane inhibitor.

52. The method of assessing an effect of a modifier on blood coagulation according to claim 44, further comprising:
 removing a coagulation component from each of the first portion of the blood sample and the second portion of the blood sample to enhance isolation of a specific aspect of a coagulation response.

53. The method of assessing an effect of a modifier on blood coagulation according to claim 52, further comprising:
 removing platelets from each of the first portion of the blood sample and the second portion of the blood sample to enhance isolation of fibrin formation.

54. A method of assessing an effect of a modifier on blood coagulation, the method comprising the acts of:
 driving a first portion of a blood sample at a substantially constant pressure through a first plurality of microchannels formed in a microfluidic device substrate;
 measuring a flow rate, or a variable correlated with flow rate, in at least one of the first plurality of microchannels while the first portion of the blood sample is moved through the first plurality of microchannels at the substantially constant pressure;
 determining a first flow rate value at an initiation of flow of the first portion of the blood sample;
 determining a first time at which a second flow rate value of the first portion of the blood sample is determined to be about twice the determined first flow rate value;
 determining a second time at which a third flow rate value of the first portion of the blood sample is determined to be about (1+e) times the determined first flow rate value;
 establishing a first coagulation model predictive of channel occlusion for the first portion of the blood sample using the first time and the second time in the relation $$\frac{Q(t)}{Q(0)} = \frac{1}{1 + e^{\frac{t - T_{qg}}{T_{qf} - T_{qg}}}}$$

wherein $T_{qf}$ is the second time and $T_{qg}$ is the first time;
 driving a second portion of the blood sample at the substantially constant pressure through a second plurality of microchannels formed in the microfluidic device substrate or another microfluidic device substrate;
 adding a modifier to one of the second portion of the blood sample or the second plurality of microchannels;
 measuring a flow rate, or a variable correlated with flow rate, in at least one of the second plurality of microchannels while the second portion of the blood sample is moved through the second plurality of microchannels at the substantially constant pressure;
 determining a first flow rate value at an initiation of flow of the second portion of the blood sample;
 determining a first time at which a second flow rate value of the second portion of the blood sample is determined to be about twice the determined first flow rate value of the second portion of the blood sample;
 determining a second time at which a third flow rate value of the second portion of the blood sample is determined to be about (1+e) times the determined first flow rate value of the second portion of the blood sample;
 establishing a second coagulation model predictive of channel occlusion for the second portion of the blood sample using the first time and the second time, for the second portion of the blood sample, in the relation $$\frac{Q(t)}{Q(0)} = \frac{1}{1 + e^{\frac{t - T_{qg}}{T_{qf} - T_{qg}}}}$$

wherein $T_{qf}$ is the second time and $T_{qg}$ is the first time; and comparing the coagulation model predictive of channel occlusion for the first portion of the blood sample to the coagulation model predictive of channel occlusion for the second portion of the blood sample to determine an effect of the modifier.

55. The method of assessing an effect of a modifier on blood coagulation according to claim 54, wherein the modifier comprises an anti-coagulant.

56. The method of assessing an effect of a modifier on blood coagulation according to claim 55, wherein the modifier comprises one of heparin, a low molecular weight heparin, a direct factor inhibitor, a direct thrombin inhibitor, an antithrombin protein, rivorxaban, apixaban, debigatran, a coumarin, hirudin, lepirudin, bivalirudin, argatroban, dabigatran, batroxobin, hementin.

57. The method of assessing an effect of a modifier on blood coagulation according to claim 55, wherein the modifier comprises a food supplement derivative.

58. The method of assessing an effect of a modifier on blood coagulation according to claim 54, wherein the modifier comprises an anti-platelet drug.

59. The method of assessing an effect of a modifier on blood coagulation according to claim 58, wherein the modifier comprises an irreversible cyclooxygenase inhibitor, an adenosine diphosphate (ADP) receptor inhibitor, a phosphodiesterase inhibitor, a glycoprotein IIb/IIIa inhibitor, an adenosine reuptake inhibitor, or a thromboxane inhibitor.

60. The method of assessing an effect of a modifier on blood coagulation according to claim 54, further comprising:
driving a third portion of the blood sample at a substantially constant pressure through a third plurality of microchannels formed in the microfluidic device substrate or another microfluidic device substrate;
adding a second modifier to one of the third portion of the blood sample or the third plurality of microchannels;
measuring a flow rate, or a variable correlated with flow rate, in at least one of the third plurality of microchannels while the third portion of the blood sample is moved through the third plurality of microchannels at the substantially constant pressure;
determining a first flow rate value at an initiation of flow of the third portion of the blood sample;
determining a first time at which a second flow rate value of the third portion of the blood sample is determined to be about twice the determined first flow rate value of the third portion of the blood sample;
determining a second time at which a third flow rate value of the third portion of the blood sample is determined to be about (1+e) times the determined first flow rate value of the third portion of the blood sample;
establishing a third coagulation model predictive of channel occlusion for the third portion of the blood sample using the first time and the second time, for the third portion of the blood sample, in the relation $$\frac{Q(t)}{Q(0)} = \frac{1}{1+e^{\frac{t-T_{qg}}{T_{qf}-T_{qg}}}}$$

wherein $T_{qf}$ is the second time and $T_{qg}$ is the first time; and
comparing the coagulation model predictive of channel occlusion for the first portion of the blood sample to the coagulation model predictive of channel occlusion for the third portion of the blood sample to determine an effect of the second modifier,
wherein the second modifier is different than the modifier.

61. The method of assessing an effect of a modifier on blood coagulation according to claim 60, wherein the second modifier is the same substance as the modifier, but comprises a different amount or concentration.

62. The method of assessing an effect of a modifier on blood coagulation according to claim 54, further comprising:
removing a coagulation component from each of the first portion of the blood sample and the second portion of the blood sample to enhance isolation of a specific aspect of a coagulation response.

63. The method of assessing an effect of a modifier on blood coagulation according to claim 62, further comprising:
removing platelets from each of the first portion of the blood sample and the second portion of the blood sample to enhance isolation of fibrin formation.

* * * * *